United States Patent
Denison et al.

(10) Patent No.: US 9,149,635 B2
(45) Date of Patent: Oct. 6, 2015

(54) STIMULATION WAVEFORM GENERATOR FOR AN IMPLANTABLE MEDICAL DEVICE

(75) Inventors: Timothy J. Denison, Minneapolis, MN (US); Robert W. Hocken, Jr., Scottsdale, AZ (US); Gabriela C. Molnar, Fridley, MN (US); Wesley A. Santa, Andover, MN (US); Jalpa S. Shah, Minneapolis, MN (US); Larry E. Tyler, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 599 days.

(21) Appl. No.: 13/458,109

(22) Filed: Apr. 27, 2012

(65) Prior Publication Data

US 2013/0289658 A1    Oct. 31, 2013

(51) Int. Cl.
*A61N 1/36*    (2006.01)
*A61N 1/378*    (2006.01)

(52) U.S. Cl.
CPC ............ *A61N 1/36125* (2013.01); *A61N 1/378* (2013.01); *A61N 1/3787* (2013.01)

(58) Field of Classification Search
CPC ....... A61N 1/08; A61N 1/36; A61N 1/36125; A61N 1/36146; A61N 1/3615; A61N 1/36153; A61N 1/36157; A61N 1/36167; A61N 1/36175; A61N 1/36178; A61N 1/378
USPC ................ 607/7, 11, 16, 34, 59, 68, 115, 116
See application file for complete search history.

(56) References Cited

U.S. PATENT DOCUMENTS

| | | | |
|---|---|---|---|
| 4,338,945 A | 7/1982 | Kosugi et al. | |
| 4,390,023 A | 6/1983 | Rise | |
| 5,318,591 A * | 6/1994 | Causey et al. | 607/5 |
| 5,370,666 A * | 12/1994 | Lindberg et al. | 607/16 |
| 5,370,672 A | 12/1994 | Fowler et al. | |
| 5,507,781 A * | 4/1996 | Kroll et al. | 607/7 |
| 5,713,939 A | 2/1998 | Nedungadi et al. | |
| 5,797,968 A * | 8/1998 | Lopin et al. | 607/5 |
| 5,836,983 A * | 11/1998 | Weijand et al. | 607/9 |
| 5,978,706 A * | 11/1999 | Brewer et al. | 607/8 |

(Continued)

FOREIGN PATENT DOCUMENTS

| | | |
|---|---|---|
| JP | 2006271907 A | 10/2006 |
| WO | 9301863 A1 | 2/1993 |

(Continued)

OTHER PUBLICATIONS

De Ridder et al., "Burst Spinal Cord Stimulation: Toward Paresthesia-Free Pain Suppression," Neurosurgery, vol. 66, No. 5, May 2010, pp. 986-990.

(Continued)

*Primary Examiner* — Carl H Layno
*Assistant Examiner* — Eugene Wu
(74) *Attorney, Agent, or Firm* — Shumaker & Sieffert, P.A.

(57) ABSTRACT

This disclosure describes techniques for generating stimulation current pulses that have differing pulse shapes in a medical device. A circuit architecture is described that is configured to charge a capacitor to an initial amount of charge, modulate the amount of charge stored in the capacitor based on a control signal, and generate a stimulation current pulse that has an amplitude based on the amount charge stored in the capacitor. The circuit architecture may be configured to generate complex pulse shapes, such as, e.g., steps, ramps, bursts, and combinations thereof.

26 Claims, 14 Drawing Sheets

(56) References Cited

U.S. PATENT DOCUMENTS

| | | | |
|---|---|---|---|
| 6,083,252 A | | 7/2000 | King et al. |
| 6,298,266 B1* | | 10/2001 | Rubin et al. ............ 607/5 |
| 6,772,007 B1* | | 8/2004 | Kroll ............ 607/7 |
| 6,950,706 B2 | | 9/2005 | Rodriguez et al. |
| 2001/0031991 A1 | | 10/2001 | Russial |
| 2002/0077670 A1* | | 6/2002 | Archer et al. ............ 607/45 |
| 2003/0125773 A1* | | 7/2003 | Havel et al. ............ 607/7 |
| 2003/0204224 A1* | | 10/2003 | Torgerson et al. ............ 607/48 |
| 2003/0212440 A1* | | 11/2003 | Boveja ............ 607/46 |
| 2005/0085862 A1* | | 4/2005 | Moulder et al. ............ 607/5 |
| 2005/0228461 A1* | | 10/2005 | Osorio et al. ............ 607/45 |
| 2006/0271110 A1* | | 11/2006 | Vernon et al. ............ 607/2 |
| 2007/0097593 A1* | | 5/2007 | Armstrong ............ 361/232 |
| 2009/0024189 A1 | | 1/2009 | Lee et al. |
| 2009/0105785 A1 | | 4/2009 | Wei et al. |
| 2010/0106223 A1 | | 4/2010 | Grevious et al. |
| 2010/0114200 A1* | | 5/2010 | Krause et al. ............ 607/4 |
| 2010/0274326 A1 | | 10/2010 | Chitre et al. |
| 2010/0318007 A1 | | 12/2010 | O'Brien |
| 2011/0276103 A1* | | 11/2011 | Maile et al. ............ 607/9 |

FOREIGN PATENT DOCUMENTS

| | | | |
|---|---|---|---|
| WO | 03047685 | A2 | 6/2003 |
| WO | 2007124074 | A2 | 11/2007 |
| WO | 2010009141 | A1 | 1/2010 |
| WO | 2011085210 | A1 | 7/2011 |

OTHER PUBLICATIONS

Foutz et al., "Evaluation of novel stimulus waveforms for deep brain stimulation," Journal of Neural Engineering, vol. 7, 2010, pp. 1-10.
Jezemik et al., "Energy-Optimal Electrical Excitation of Nerve Fibers." IEEE Transactions on Biomedical Engineering, vol. 52, No. 4, Apr. 2005 pp. 740-743.
Sahin et al., "Non-rectangular waveforms for neural stimulation with practical electrodes," Journal of Neural Engineering, vol. 4, 2007, pp. 227-233.
Wongsarnpigoon et al., "Efficiency Analysis of Waveform Shape for Electrical Excitation of Nerve Fibers," IEEE Transactions on Neural Systems and Rehabilitation Engineering, vol. 18, No. 3, Jun. 2010, pp. 319-328.
Wongsarnpigoon et al., "Energy-efficient waveform shapes for neural stimulation revealed with a genetic algorithm," Journal of Neural Engineering, vol. 7, 2010, pp. 1-11.
Bhadra et al., "High frequency electrical conduction block of the pudendal nerve," Journal of Neural Engineering, vol. 3, 2006, pp. 180-187.
Birdno et al., "Tremor varies as a function of the temporal regularity of deep brain stimulation," Neuroreport, Mar. 2008, 8 pages.
Birdno et al., "Pulse-to-Pulse Changes in the Frequency of Deep Brain Stimulation Affect Tremor and Modeled Neuronal Activity," J. Neurophysiol 98(3), 2007, pp. 1675-1684.
Grill et al., "Stimulus Waveforms for Selective Neural Stimulation," IEEE Engineering in Medicine and Biology, Jul./Aug. 1995, pp. 375-385.
Qin et al., "Subthalamic coordinated reset stimulation has sustained effects on motor symptoms in MPTP treated non-human primates," abstract #226, Movement Disorders, vol. 26., Suppl. 2, 2011, pp. S74-S75.
Tai et al., "Block of External Urethral Sphincter Contraction by High Frequency Electrical Stimulation of Pudendal Nerve," The Journal of Urology, vol. 172, 2004, pp. 2069-2072.
Soin et al., "Usage of High Frequency Alternating Current (HFAC) in the Treatment of Chronic Pain Disorders," North American Neuromodulation Society, 2009, 1 page.
Dinsmoor et al., "Neurostimulation Design from an Energy and Information Transfer Perspective," Bio-medical CMOS ICs, Yoo & Hoof (eds.) New York, NY: Springer, 2010, 30 pages.
Paralikar et al., "An Implantable Optical Stimulation Delivery System for Actuating an Excitable Biosubstrate," IEEE Journal of Solid-State Circuits, vol. 46, No. 1, Jan. 2011, pp. 321-332.
International Search Report and Written Opinion of the International Searching Authority for corresponding patent application No. PCT/US2013/034079, mailed Jun. 14, 2013, 12 pages.

* cited by examiner

STIMULATION WAVEFORM GENERATOR FOR AN IMPLANTABLE MEDICAL DEVICE

TECHNICAL FIELD

The disclosure relates to medical devices and, more particularly, to medical devices that deliver electrical stimulation to a patient.

BACKGROUND

A variety of medical devices are used for chronic, e.g., long-term, delivery of electrical stimulation therapy to patients suffering from conditions that range from chronic pain, tremor, Parkinson's disease, and epilepsy, to urinary or fecal incontinence, sexual dysfunction, obesity, spasticity, and gastroparesis. As an example, electrical stimulation generators are used for chronic delivery of electrical stimulation therapies such as neurostimulation, spinal cord stimulation, muscle stimulation, target organ stimulation, or the like. Typically, such devices provide therapy continuously or periodically according to parameters contained within a program. A program may comprise respective values for each parameter in a set of therapeutic parameters specified by a clinician. For example, a program may define characteristics of the electrical pulses defining the stimulation waveform, including pulse width, pulse frequency, constant voltage or constant current amplitude, and electrode polarity (anode or cathode). Traditional neurological stimulators generate a constant voltage or constant current output pulse that is typically programmable for a predefined constant current or voltage stimulus amplitude and pulse width.

SUMMARY

This disclosure describes techniques for generating stimulation current pulses that have differing pulse shapes in a medical device. For example, a circuit architecture is described that is configured to generate a stimulation current pulse that has a programmable pulse shape. The techniques of this disclosure may include generating a stimulation current pulse such that the pulse has an amplitude that is determined based on an amplitude of a first control signal that is sampled at or prior to the time delivery of a stimulation pulse begins, and a second control signal that is monitored during the delivery of the stimulation current pulse. The second control signal may vary with respect to time during the delivery of the stimulation current pulse. The first control signal may be used to control a fixed amplitude component of the stimulation current pulse that may remain substantially fixed during delivery of the stimulation current pulse, and the second control signal may be used to control a time-varying amplitude component of the stimulation current pulse that may vary during delivery of the stimulation current pulse. In some examples, the first control signal may be used to charge a capacitor to an initial amount of charge, and the second control signal may be used to modulate the amount of charge stored in the capacitor during the delivery of a stimulation current pulse. The amplitude of the stimulation current pulse may be determined based on the amount of charge stored in the capacitor. One or both of the first and second control signals may be programmatically controlled to achieve a particular stimulation pulse shape. The techniques described herein may be configured to generate complex pulse shapes including, for example, step-shaped pulses, ramp-shaped pulses, burst-shaped pulses, or any combination thereof.

In one aspect, this disclosure is directed to a method that includes coupling a first signal to a terminal of a capacitor in a medical device. The method further includes charging the capacitor such that the capacitor stores an amount of charge indicative of an amplitude of the first signal. The method further includes decoupling the first signal from the terminal of the capacitor at a point in time. The method further includes, while the first signal is decoupled from the capacitor, modulating the amount of charge stored in the capacitor based on a second signal that varies with respect to time during delivery of a stimulation current pulse such that the capacitor stores a modulated amount of charge that is a function of the amplitude of the first signal at the point in time and a function of the second signal. The method further includes, while the first signal is decoupled from the capacitor, generating the stimulation current pulse such that the stimulation current pulse has an amplitude that is determined based on the modulated amount of charge stored in the capacitor and that varies with respect to time based on the second signal.

In another aspect, this disclosure is directed to a medical device that includes a stimulation generator circuit configured to couple a first signal to a terminal of a capacitor. The stimulation generator circuit is further configured to charge the capacitor such that the capacitor stores an amount of charge indicative of an amplitude of the first signal. The stimulation generator circuit is further configured to decouple the first signal from the terminal of the capacitor at a point in time. The stimulation generator circuit is further configured to, while the first signal is decoupled from the capacitor, modulate the amount of charge stored in the capacitor based on a second signal that varies with respect to time during delivery of a stimulation current pulse such that the capacitor stores a modulated amount of charge that is a function of the amplitude of the first signal at the point in time and a function of the second signal. The stimulation generator circuit is further configured to, while the first signal is decoupled from the capacitor, generate the stimulation current pulse such that the stimulation current pulse has an amplitude that is determined based on the modulated amount of charge stored in the capacitor and that varies with respect to time based on the second signal.

In another aspect, this disclosure is directed to a medical device that includes a stimulation generator circuit. The stimulation generator circuit includes a capacitor and is configured to couple a first signal to a terminal of the capacitor. The stimulation generator circuit is further configured to charge the capacitor such that the capacitor stores an amount of charge indicative of an amplitude of the first signal. The stimulation generator circuit is further configured to decouple the first signal from the terminal of the capacitor at a point in time. The stimulation generator circuit is further configured to, while the first signal is decoupled from the capacitor, modulate the amount of charge stored in the capacitor based on a second signal that varies with respect to time during delivery of a stimulation current pulse such that the capacitor stores a modulated amount of charge that is a function of the amplitude of the first signal at the point in time and a function of the second signal. The stimulation generator circuit is further configured to, while the first signal is decoupled from the capacitor, generate the stimulation current pulse such that the stimulation current pulse has an amplitude that is determined based on the modulated amount of charge stored in the capacitor and that varies with respect to time based on the second signal.

In another aspect, this disclosure is directed to a medical device that includes means for coupling a first signal to a terminal of a capacitor. The medical device further includes means for charging the capacitor such that the capacitor stores an amount of charge indicative of an amplitude of the first signal. The medical device further includes means for decoupling the first signal from the terminal of the capacitor at a point in time. The medical device further includes means for modulating, while the first signal is decoupled from the capacitor, the amount of charge stored in the capacitor based on a second signal that varies with respect to time during delivery of a stimulation current pulse such that the capacitor stores a modulated amount of charge that is a function of the amplitude of the first signal at the point in time and a function of the second signal. The medical device further includes means for generating, while the first signal is decoupled from the capacitor, the stimulation current pulse such that the stimulation current pulse has an amplitude that is determined based on the modulated amount of charge stored in the capacitor and that varies with respect to time based on the second signal.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
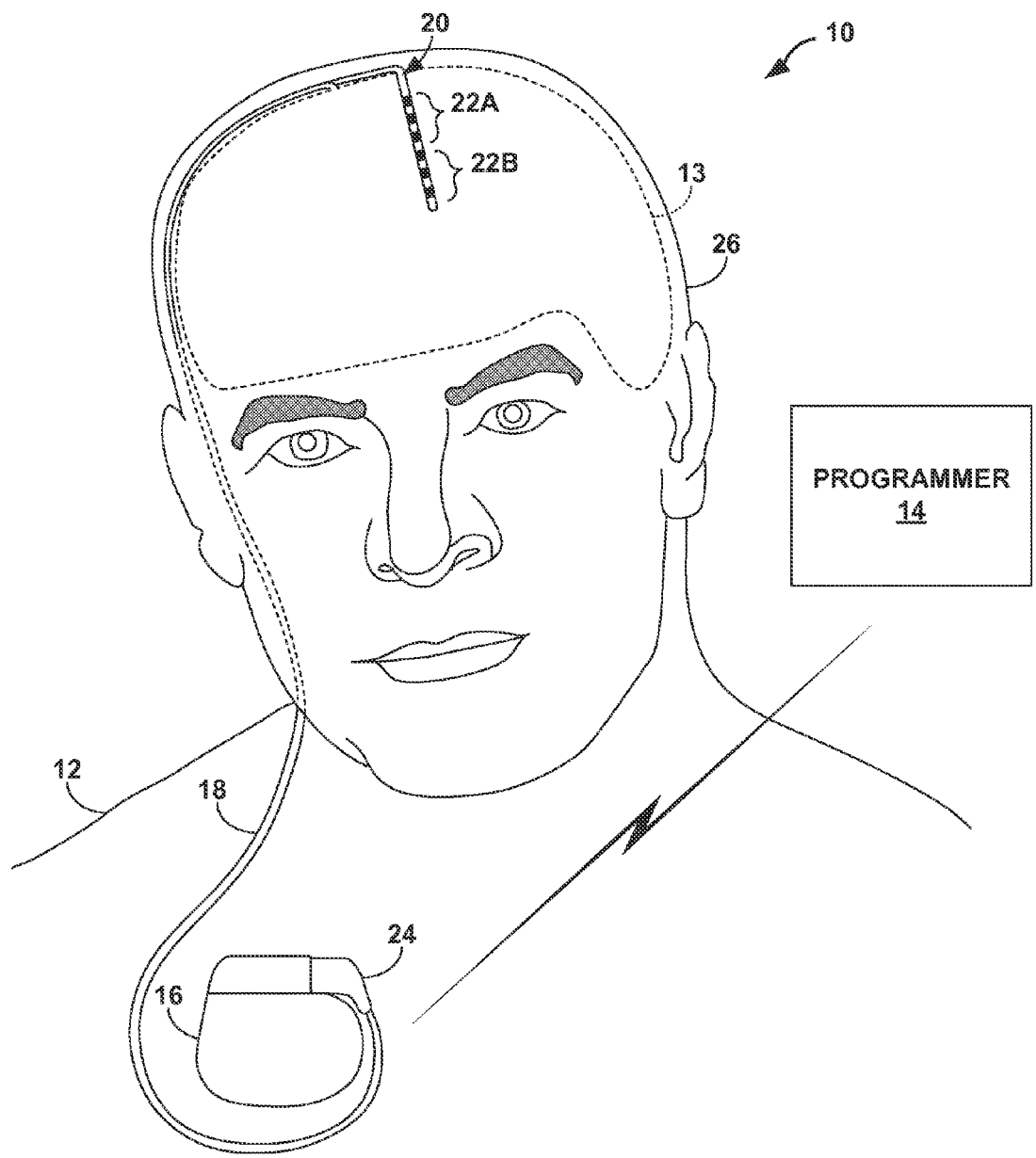
FIG. 1 is a conceptual diagram illustrating an example of an implantable electrical stimulation system that may implement stimulation waveform generation techniques in accordance with this disclosure.

This disclosure describes techniques for generating stimulation current pulses that have differing pulse shapes in a medical device. For example, a circuit architecture is described that is configured to generate a stimulation current pulse that has a programmable pulse shape. The techniques of this disclosure may include generating a stimulation current pulse such that the pulse has an amplitude that is determined based on an amplitude of a first control signal that is sampled at or prior to the time delivery of a stimulation pulse begins, and a second control signal that is monitored during the delivery of the stimulation current pulse. The second control signal may vary with respect to time during the delivery of the stimulation current pulse. The first control signal may be used to control a fixed amplitude component of the stimulation current pulse that may remain substantially fixed during delivery of the stimulation current pulse, and the second control signal may be used to control a time-varying amplitude component of the stimulation current pulse that may vary during delivery of the stimulation current pulse. In some examples, the first control signal may be used to charge a capacitor to an initial amount of charge, and the second control signal may be used to modulate the amount of charge stored in the capacitor during the delivery of a stimulation current pulse. The amplitude of the stimulation current pulse may be determined based on the amount of charge stored in the capacitor. One or both of the first and second control signals may be programmatically controlled to achieve a particular stimulation pulse shape. The techniques described herein may be configured to generate complex pulse shapes including, for example, step-shaped pulses, ramp-shaped pulses, burst-shaped pulses, or any combination thereof.

One technique for generating a stimulation current in an implantable medical device is to use a continuous time feedback based current mirror architecture. Although such an architecture may allow the magnitude of an output current to be instantaneously updated during the delivery of a stimulation pulse by adjusting the input current during the delivery of the pulse, such an architecture is typically difficult to bias properly. For example, complex circuitry may be needed to bias the feedback loop properly and/or the settling times needed to achieve a proper biasing may be significant. In addition, a continuous time feedback based current mirror architecture requires that the input current be provided for the entire duration of the stimulation pulse to control the amplitude of the pulse.

In order to overcome the drawbacks of a continuous time feedback based current mirror architecture, a non-continuous time feedback based current mirror architecture may be used. Such a circuit architecture may operate by switching between a precharge phase and a stimulation phase. During the precharge phase, the input current may be applied to the circuit to efficiently and accurately bias the feedback loop prior to the stimulation phase. At the end of the precharge phase, a voltage corresponding to the input current may be sampled and applied to the feedback loop. During the stimulation phase, an output current is generated having a magnitude that corresponds to the sampled voltage. By dividing the operation of the circuit into precharge and stimulation phases, such a circuit may be accurately and efficiently biased during the precharge phase. Moreover, the input current need not be provided to such a circuit during the stimulation phase, thereby allowing the current source for the input current to be powered down. As such, the non-continuous time feedback based circuit architecture overcomes the drawbacks of the continuous time feedback based current mirror architecture discussed above. However, because the non-continuous time feedback based circuit uses a sampled voltage corresponding to the input current during the stimulation phase, the amplitude of the output current cannot be instantaneously adjusted during the stimulation phase by merely adjusting the input current. Such a limitation hinders the ability of such as a circuit to generate a stimulation waveform having complex waveform pulse shapes, such as steps, ramps and bursts.

The disclosure describes techniques for allowing a non-continuous time feedback based circuit architecture to instantaneously adjust the amplitude of an output current during the delivery of a stimulation pulse in order to generate different pulse shapes. Such techniques may allow complex pulse shapes to be generated while still obtaining one or more of the benefits of a non-continuous time feedback based architecture. That is, the techniques may, in some examples, allow efficient and accurate biasing of the circuit and need not require the input current signal to be continuously asserted during the stimulation phase.

In some examples, a stimulation generator circuit designed in accordance with this disclosure may include a capacitor in a feedback loop of the circuit, and the stimulation generator circuit may generate a stimulation current pulse having an amplitude that is determined based on the amount of charge stored in the capacitor. In such examples, during a precharge phase, the stimulation generator circuit may couple a first control signal to the capacitor, and the capacitor may be charged such that the resulting amount of charge stored in the capacitor is indicative of the amplitude of the first signal. When the stimulation generator circuit switches from the precharge phase to the stimulation phase, the stimulation generator circuit may decouple the first signal from the capacitor, thereby causing the first signal to be sampled. During the stimulation phase, the stimulation generator circuit may modulate the charge stored in the capacitor based on a second control signal to adjust the amplitude of the stimulation current pulse. Because the second signal may be used to adjust the amplitude of the stimulation current during the delivery of a stimulation pulse, such a circuit is able to generate complex waveform pulse shapes even though a baseline amplitude determined by the first signal may be sampled for each pulse.

In some examples, a capacitive digital-to-analog converter (CAPDAC) may be electrically coupled to the capacitor in the feedback loop that controls the amplitude of the stimulation current. The CAPDAC may include a plurality of capacitors each of which may have a terminal that may be selectively switched between a high voltage and a low voltage. The switching state of the CAPDAC may be modified based on the second control signal. The capacitors in the CAPDAC may form a capacitance network with the capacitor in the feedback loop. The capacitance network may distribute the charge among the capacitors in the network, including the feedback loop capacitor, based on a switching state of the CAPDAC. Therefore, when the second signal modifies the state of the CAPDAC, in such examples, the charge stored in the feedback loop capacitor may be modified, which may in turn cause the amplitude of the resulting stimulation current to be modified.

Because the techniques of this disclosure sample a first control signal at or prior to the time delivery of a stimulation pulse begins, the techniques of this disclosure may allow a signal generator that generates the first control signal to be powered down during the delivery of a stimulation pulse. In this manner, the techniques of this disclosure may reduce the power consumption of an implantable medical device in comparison to implantable medical devices that use continuous-time current sources that require input signals to be maintained throughout the entire duration of the stimulation pulse.

For example, the first signal may be generated using a resistive digital-to-analog converter (DAC). In such an example, the resistive DAC may provide a baseline amplitude component for the stimulation pulse while the CAPDAC may be programmed to provide a time-varying component for the stimulation pulse. In some cases, the resistive DAC may consume more power than the CAPDAC. However, the techniques of this disclosure may allow the resistive DAC to be powered down during the delivery of the stimulation pulse, thereby reducing the power consumption of the IMD while still providing the ability to generate complex waveform pulse shapes.

In some examples, the techniques of this disclosure may utilize a feedback circuit architecture that allows an output transistor to operate in a linear operating mode during the delivery of a stimulation pulse. Allowing the output transistor to operate in the linear operating mode, as opposed to in a saturation operating mode, may reduce voltage headroom requirements and improve efficiency in certain types of operating conditions.

In additional examples, the techniques of this disclosure may be implemented in a feedback sense resistor based architecture where a baseline current is applied through a reference resistor in order to generate the first signal, and the output current is generated based on a voltage across a sense resistor. In such examples, the matching between the amplitude of the baseline current and the fixed amplitude component of the output current may, in some cases, be driven by the matching of the sense and reference resistors rather than by the matching of transistors.

In further examples, one or both of the first and second control signals may be programmable to generate signals having particular amplitudes and/or shapes. For example, in response to receiving information indicative of a selected pulse shape, the IMD may program one or both of the first and second control signals such that the signals will cause the stimulation generator circuit to generate a stimulation waveform having the selected pulse shape. In some cases, the first control signal may be programmed to have an amplitude that is based on a user-selected baseline amplitude for the stimulation pulse. In additional cases, the second control signal may include a sequence of program codes, and the IMD may program the second signal by selecting a particular sequence of program codes that corresponds to the selected pulse shape. In such cases, the stimulation generator circuit may be configured to retrieve program codes from a memory at particular time intervals during the delivery of a stimulation pulse, and update the amplitude of the resulting stimulation current based on the retrieved program codes.

FIG. 1 is a conceptual diagram illustrating an example of an implantable electrical stimulation system that may implement stimulation waveform generation techniques in accordance with this disclosure. In FIG. 1 the example implantable electrical stimulation system is a deep brain stimulation (DBS) system 10 that manages a medical condition of a patient 12. Patient 12 ordinarily will be a human patient. In some cases, however, DBS system 10 may be applied to other mammalian or non-mammalian non-human patients. DBS system 10 may provide therapy to patient 12 in order to minimize the severity or duration of one or more patient conditions, and, in some cases, in order to eliminate symptoms associated with a patient condition. DBS system 10 includes medical device programmer 14, implantable medical device (IMD) 16, lead extension 18, lead 20 with respective electrodes 22A and 22B (collectively referred to as "electrodes 22") and connector block 24. For ease of description examples of the disclosure are primarily described with regard to DBS system 10. However, examples of the disclosure are not limited as such and may include any medical system or device suitable for implementing one or more of the examples techniques described in this disclosure.

IMD 16 of system 10 includes a therapy module that delivers electrical stimulation therapy to one or more regions of brain 13 via lead 20. In the example shown in FIG. 1, system 10 may be referred to as a deep brain stimulation (DBS) system because IMD 16 provides electrical stimulation therapy directly to tissue within brain 13, such as under the dura mater of brain 13. In addition to or instead of deep brain sites, IMD 16 may deliver electrical stimulation to target tissue sites on a surface of brain 13, such as between the patient's cranium and the dura mater of brain 13 (e.g., the cortical surface of brain 13).

For ease of illustration, examples of the disclosure are primarily described with regard to the delivery of electrical stimulation therapy to brain 13 of patient 12 by IMD 16. However, in other examples, an IMD or other medical device may deliver electrical stimulation therapy to one or more nerve sites and/or one more muscle sites of patient 12 in addition to or in lieu of brain 13. For example, IMD 16 may deliver spinal cord stimulation (SCS) to patient 12, e.g., via one or more leads implanted adjacent to the spinal cord of patient 12. The electrical stimulation may be delivered to ventral (anterior) sites to block or disrupt motor output from the spinal cord (not shown) of patient 12, e.g., to disrupt the limb movement of patient 12. As another example, IMD 16 may deliver electrical stimulation to one or more muscle sites of patient 12 to inhibit patient movement. In general, electrical stimulation may be delivered to patient 12 via one or more electrodes implanted in or located external to patient 12 via one or more implanted or external medical devices.

According to this disclosure IMD 16 may include a stimulation generation circuit that is configured to generate stimulation current waveforms that have differing pulse shapes. The waveform pulse shapes generated by IMD 16 may include complex shapes, such as, e.g., ramps, steps and bursts. In some examples, IMD 16 may receive information that is indicative of a selected waveform pulse shape (e.g., a pulse shape selected by a user) from programmer 14, and program the stimulation generation circuit to generate a waveform having the selected waveform pulse shape.

In some examples, the stimulation generation circuit may be configured to sample an amplitude of a first signal, receive a second signal that varies with respect to time, and generate a stimulation current pulse having an amplitude that is determined based on the sampled amplitude of the first signal and the second signal. The amplitude of the stimulation current pulse may vary with respect to time during delivery of the stimulation current pulse based on the second signal.

In further examples, the stimulation generator circuit may be configured to couple a first signal to a terminal of a capacitor, charge the capacitor such that the capacitor stores an amount of charge indicative of an amplitude of the first signal, and decouple the first signal from the terminal of the capacitor at a point in time. After decoupling the first signal from the terminal of the capacitor, the stimulation generator circuit may be configured to modulate the amount of charge stored in the capacitor based on a second signal that varies with respect to time during delivery of a stimulation current pulse such that the capacitor stores a modulated amount of charge that is a function of the amplitude of the first signal at the point in time and a function of the second signal. While the first signal is decoupled from the capacitor, the stimulation generator circuit may be configured to generate the stimulation current pulse such that the stimulation current pulse has an amplitude that is determined based on the modulated amount of charge stored in the capacitor and that varies with respect to time based on the second signal. Further details regarding the construction and operation of an example stimulation generation circuit designed in accordance with this disclosure are described with respect to FIGS. 4-12.

IMD 16 may be constructed of a biocompatible material that resists corrosion and degradation from bodily fluids. IMD 16 may comprise a hermetic housing or a near hermetic housing to substantially enclose components, such as a processor, therapy module, and memory. In one example IMD 16 may have a volume of approximately 3 cubic centimeters (cc) to approximately 14 cc. In the example shown in FIG. 1, IMD 16 may be implanted within a chest cavity of patient 12 or within a subcutaneous pocket below the clavicle that is over the chest cavity of patient 12. In other examples, IMD 16 may be implanted within other regions of patient 12, such as a subcutaneous pocket in the abdomen of patient 12 or proximate to the cranium of patient 12. Implanted lead extension 18 is mechanically and electrically connected to IMD 16 via connector block 24, which may include, for example, electrical contacts that electrically couple to respective electrical contacts on lead extension 18. The electrical contacts electrically couple the electrodes 22A and 22B (collectively "electrodes 22") on lead 20 to IMD 16. Lead extension 18 traverses from the implant site of IMD 16 within patient 12, along the neck of patient 12 and through the cranium of patient 12 to access brain 13.

Although lead 20 is shown in FIG. 1 as a single lead, in other examples lead 20 may include multiple leads implanted within brain 13 of patient 12 to treat one or more disorders of patient 12. Lead 20 may be implanted within the right and/or left hemispheres of brain 13 in order deliver electrical stimulation to one or more regions of brain 13, which may be selected based on many factors, such as the type of patient condition for which DBS system 10 is implemented to manage. In addition, electrodes 22 on lead 20 may, in some examples, be used to sense brain activity. Different neurological or psychiatric disorders may be associated with activity in one or more regions of brain 13, which may differ between patients.

Although lead 20 is shown in FIG. 1 as being coupled to IMD 16 via lead extension 18, in other examples, lead 20 may be directly coupled to IMD 16. Lead 20 may deliver electrical stimulation to treat any number of psychiatric or neurological disorders or diseases. For example, IMD 16 may deliver electrical stimulation therapy via electrodes 22 on lead 20 to brain 13 of patient 12 to treat a movement disorder such as tremor, Parkinson's disease (PD), multiple sclerosis, or spasticity. Examples of psychiatric disorders that may be treated by delivery of electrical stimulation from IMD 16 to brain 13 of patient 12 may include major depressive disorder, anxiety, hypomania or bipolar disorder.

Lead 20 may be implanted within a desired location of brain 13 via any suitable technique, such as through a burr hole in a skull of patient 12. Lead 20 may be placed at any location within brain 13 such that the electrodes of the leads are capable of providing electrical stimulation to targeted tissue during treatment. Electrical stimulation generated by a stimulation generator (not shown) of IMD 16 and delivered to brain 13 of patient 12 may help to prevent the onset of symptoms or mitigate the symptoms associated with a patient's neurological disorder being treated by DBS system 10.

In some examples, lead 20 may be implanted such that electrodes 22B (or some electrodes positioned distally on lead 20) are capable of delivering electrical stimulation to the pedunculopontine nucleus (PPN) or other midbrain nuclei, while electrode 22A (or other electrodes positioned more proximally on lead 20) are capable of delivering electrical stimulation to the globus pallidus interna (GPi) and/or other basal ganglia such as the subthalamic nucleus (STN). In this manner, IMD 16 may deliver stimulation to multiple tissue sites via a single lead. In some examples, one or both of the target tissue sites may be used to treat other patient disorders, such as, e.g., Parkinson's disease.

The exact stimulation therapy parameter values of the stimulation therapy, such as the amplitude or magnitude of the stimulation signals, the duration of each signal, the waveform of the stimuli, the frequency of the signals, and the like, may be specific for the particular target stimulation site (e.g., a particular region of the brain) as well as the particular patient and/or patient condition.

In the case of stimulation pulses, the stimulation therapy may be characterized by selected pulse parameters, such as, e.g., pulse amplitude (e.g., a voltage amplitude or a current amplitude), pulse rate, and/or pulse width. In addition, if different electrodes are available for delivery of stimulation, the therapy may be further characterized by different electrode combinations. Stimulation parameters may be selected to treat one or more symptoms of a patient disorder.

Electrodes 22 may be arranged in a unipolar, bipolar, or multipolar arrangement for delivery of stimulation. A unipolar stimulation arrangement generally refers to the use of an anode on the housing of IMD 16 that sources current and one or more cathodes on one or more leads that sink current. A bipolar stimulation arrangement generally refers to the use of an anode on a lead that sources current and a cathode on the same lead and/or another lead that sinks current. A multipolar stimulation arrangement generally refers to the use of two or more anodes on a lead that each source current and one or more cathodes on the same lead or another lead that sink current, or the use of one anode on a lead that sources current and two or more cathodes on the same lead or another lead that sink current.

Electrodes 22 of lead 20 are shown as ring electrodes. Ring electrodes may be relatively easy to program and are typically capable of delivering an electrical field to any tissue adjacent to lead 20. In other examples, electrodes 22 of lead 20 may have different configurations. For example, electrodes 22 of lead 20 may have a complex electrode array geometry that is capable of producing electrical fields having predefined shapes, e.g., shapes that are selected based on target tissue sites within brain 13 for the electrical stimulation. The complex electrode array geometry may include multiple electrodes (e.g., partial ring or segmented electrodes) around the perimeter of lead 20, rather than a ring electrode. In this manner, electrical stimulation may be directed in a specific direction from lead 20 to enhance therapy efficacy and reduce possible adverse side effects from stimulating a large volume of tissue. In some examples, a housing of IMD 16 may include one or more stimulation and/or sensing electrodes. In alternative examples, lead 20 may have a shape other than the elongated cylinder shown in FIG. 1. For example, lead 20 may be a paddle lead, spherical lead, bendable lead, or any other type of shape effective in treating patient 12.

In some examples, one or more of electrodes 22 on lead 20 may be used to sense electrical signals within one or more regions of brain 13. Alternatively, an additional set of sensing electrodes (not shown) may be used to monitor the electrical signals in brain 13. In general, the electrical signals within brain 13 may be interchangeably referred to herein as biosignals or bioelectrical brain signals. The biosignal may include a bioelectrical signal, such as an electroencephalogram (EEG) signal, an electrocorticogram (ECoG) signal, a local field potential (LFP) sensed from within one or more regions of brain 13, and/or action potentials from single cells within brain 13. For example, a sensed brain signal may include an EEG signal, which may be generated via one or more electrodes implanted and/or located external to patient 12. Electrodes implanted closer to a target region of brain 13 may help generate an electrical signal that provides more useful information than an EEG generated via a surface electrode array because of the proximity to brain 13. The EEG signal that is generated from an electrode array implanted within brain 13 may also be referred to as an ECoG signal.

Programmer 14 is an external computing device that a user, e.g., the clinician and/or patient 12, may use to communicate with IMD 16. For example, programmer 14 may be a clinician programmer that a clinician uses to communicate with IMD 16 and program one or more therapy programs for IMD 16. Alternatively, programmer 14 may be a patient programmer that allows patient 12 to select programs, view electrical stimulation parameters, and/or modify electrical stimulation parameters. In some examples, programmer 14 may receive, via a user interface, a selection indicative of a particular waveform pulse shape to use for stimulation, and provide information indicative of the selected waveform pulse shape to IMD 16. The clinician programmer may, in some examples, include more programming features than the patient programmer. In other words, certain types of complex and/or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, then one or more of the buttons may, in some cases, be dedicated to performing a certain function, e.g., a power button. In additional cases, one or more of the buttons and/or the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device rather than a dedicated computing device. For example, the multi-function device may be a notebook computer, a tablet computer, a workstation, a cellular phone, a personal digital assistant (PDA) or another computing device. The multi-function device may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include information, such as the type of lead 20, the electrode 22 arrangement, the position of lead 20 within brain 13, the configuration of electrode array 22, initial programs defining electrical stimulation parameter values, and any other information the clinician desires to program into IMD 16. Programmer 14 may also be capable of completing functional tests (e.g., measuring the impedance of electrodes 22).

Programmer 14 may be used by a clinician to control delivery of electrical stimulation, such as by activating electrical stimulation, deactivating electrical stimulation, or adjusting one or more stimulation parameters of therapy being delivered to patient 12. The clinician may also store therapy programs within IMD 16 with the aid of programmer 14. During a programming session, the clinician may determine one or more therapy programs that may provide efficacious therapy to patient 12 to address symptoms associated with a disorder of patient 12. Patient 12 may provide feedback to the clinician as to the efficacy of the specific program being evaluated.

Programmer 14 may also be configured to be used by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain electrical stimulation parameters or set an available range of values for a particular electrical stimulation parameter.

Programmer 14 may also provide various indications to patient 12 to alert patient 12 of various operating conditions of IMD 16. For example, programmer 14 may provide an indication of when therapy is being delivered, when a patient input has triggered a change in electrical stimulation parameters or when a power source within programmer 14 and/or IMD 16 needs to be replaced or recharged. For example, programmer 14 may include an alert LED that may flash a message to patient 12 via a programmer display, or may generate an audible sound or somatosensory cue to confirm patient input was received, e.g., to indicate a patient state or to manually modify an electrical stimulation parameter.

Whether programmer 14 is configured for clinician or patient use, programmer 14 is configured to communicate to IMD 16 and, optionally, another computing device, via wireless communication. Programmer 14 may, for example, communicate via wireless communication with IMD 16 using radio frequency (RF) telemetry techniques known in the art. Programmer 14 may also communicate with another programmer or computing device via a wired or wireless connection using any of a variety of local wireless communication techniques, such as, e.g., RF communication according to the 802.11 or Bluetooth™ specification sets, infrared (IR) communication according to the The Infrared Data Association (IRDA) specification set, or other standard or proprietary telemetry protocols. In additional examples, programmer 14 may communicate with other programming or computing devices via exchange of removable media, such as magnetic or optical disks, memory cards or memory sticks. In further examples, programmer 14 may communicate with IMD 16 and another programmer via remote telemetry techniques, a local area network (LAN), a wide area network (WAN), a public switched telephone network (PSTN), or a cellular telephone network, for example.

DBS system 10 may be implemented to provide chronic stimulation therapy to patient 12 over the course of several months or years. However, DBS system 10 may also be employed on a trial basis to evaluate therapy before committing to full implantation. If implemented temporarily, some components of system 10 may not necessarily be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
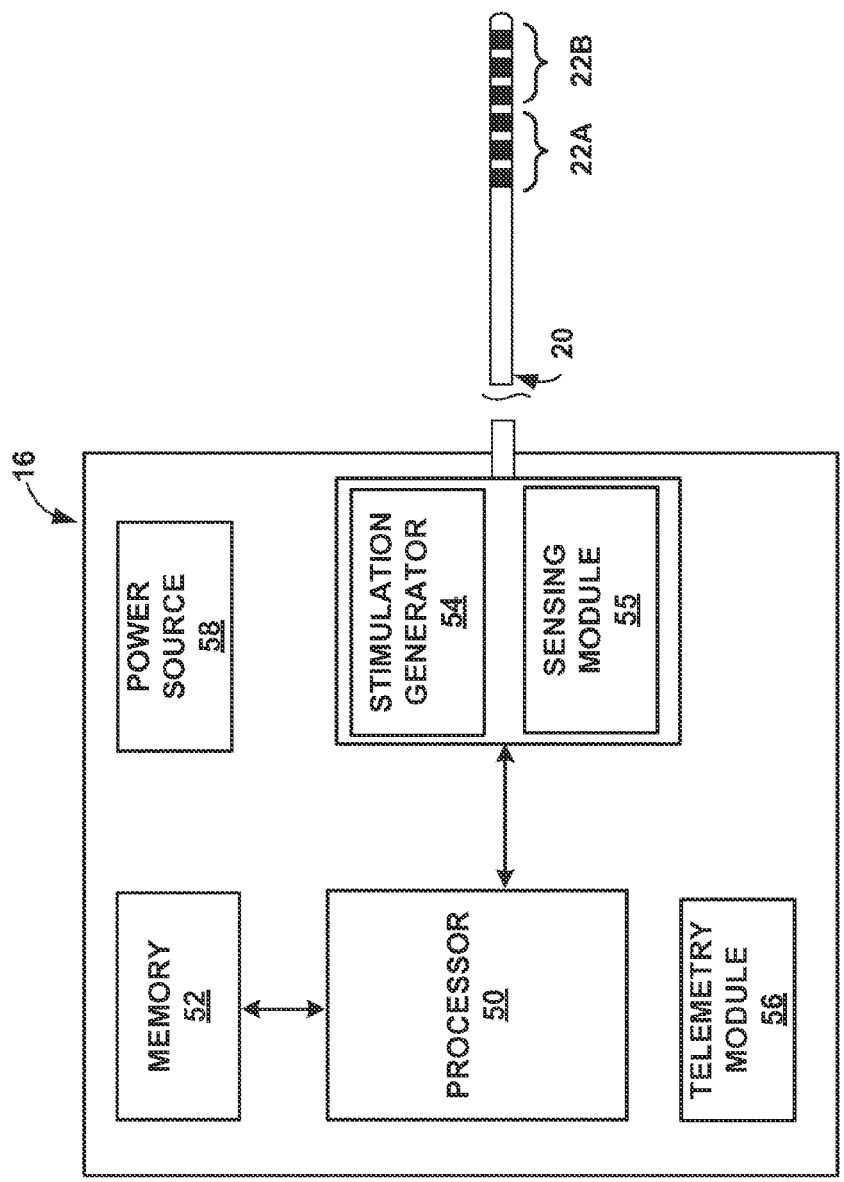
FIG. 2 is a functional block diagram illustrating the example implantable medical device of FIG. 1 in greater detail.

FIG. 2 is a functional block diagram illustrating the example IMD 16 of FIG. 1 in greater detail. In the example shown in FIG. 2, IMD 16 generates and delivers electrical stimulation therapy to patient 12. IMD 16 includes a processor 50, a memory 52, a stimulation generator 54, a sensing module 55, a telemetry module 56, and a power source 58. Although sensing module 55 is shown to be a component of IMD 16 in FIG. 2, in other examples, sensing module 55 and IMD 16 may be separate devices and may be electrically coupled, e.g., via a wired or wireless connection.

Memory 52 may include any volatile or non-volatile media, such as a random access memory (RAM), a read only memory (ROM), a non-volatile RAM (NVRAM), electrically erasable programmable ROM (EEPROM), flash memory, and the like. Memory 52 may store instructions for execution by processor 50 and information defining delivery of electrical stimulation to patient 12, such as, but not limited to, therapy programs (e.g., sets of stimulation parameter values) or therapy program groups, information associating therapy programs with one or more sleep stages, and any other information regarding the delivery of therapy to patient 12. Therapy information may be recorded in memory 52 for long-term storage and retrieval by a user. Memory 52 may include separate memories for storing information, such as separate memories for therapy programs, diagnostic information, target tissue site information, and patient information. In some examples, memory 52 stores program instructions that, when executed by processor 50, cause IMD 16 and/or processor 50 to perform the functions attributed to them herein.

Memory 52 may be considered, in some examples, a non-transitory computer-readable storage medium comprising instructions that cause one or more processors, such as, e.g., processor 50, to implement one or more of the example techniques described in this disclosure. The term "non-transitory" may indicate that the storage medium is not embodied in a carrier wave or a propagated signal. However, the term "non-transitory" should not be interpreted to mean that memory 52 is non-movable. As one example, memory 52 may be removed from IMD 16, and moved to another device. In certain examples, a non-transitory storage medium may store data that can, over time, change (e.g., the non-transitory storage medium may be a RAM).

Processor 50 controls stimulation generator 54 to deliver electrical stimulation therapy to brain 13 of patient 12 via lead 20. As described above, processor 50 may control stimulation generator 54 to generate and deliver electrical stimulation to one or more tissue sites of brain 13. Processor 50 may also control delivery of electrical stimulation to patient 12 by delivering electrical stimulation to one target tissue site with particular electrodes (e.g., electrodes 22A of DBS system 10) and to another target tissue site with different electrodes (e.g., electrodes 22B of DBS system 10). In some cases, electrical stimulation may be delivered via electrodes 22A according to a particular therapy program and via electrodes 22B according to a different therapy program. Electrical stimulation via electrodes 22A and 22B may be controlled independently, and may be controlled and delivered either simultaneously or alternatively. In other examples, processor 50 may control delivery of electrical stimulation by delivering electrical stimulation to several different target tissue sites with some or all of the same electrodes.

Processor 50 may include, for example, any one or more of a microprocessor, a controller, a digital signal processor (DSP), an application specific integrated circuit (ASIC), a field-programmable gate array (FPGA), and discrete logic circuitry. The functions attributed to processor 50 herein may be embodied as firmware, hardware, software or any combination thereof. In general, components described as processors within IMD 16, external programmer 14 or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and embodied as software, firmware, hardware, or any combination thereof.

In some examples, sensing module 55 may generate a signal indicative of electrical activity within brain 13 of patient 12 using one or more of electrodes 22 as sense electrodes, as shown in FIG. 2. In this way, sensing module 55 may detect or sense a biosignal within brain 13 of patient 12. Although FIG. 2 illustrates sensing module 55 as being incorporated into a common housing with stimulation generator 54 and processor 50, in other examples, sensing module 55 may be in a separate housing from IMD 16 and may communicate with processor 50 via wired or wireless communication techniques. Sensing module 55 may use the same or different electrodes to sense one or more biosignals of brain 13 as that which are used to deliver electrical stimulation generated by stimulation generator 54 to patient 12.

Sensing module 55 is configured to generate an electrical signal indicative of activity within brain 13 of patient 12 and/or of other physiological parameters of patient 12. As previously indicated, example electrical signals that sensing module 55 may sense include, but are not limited to, a signal generated from local field potentials within one or more regions of brain 13. EEG and ECoG signals are examples of local field potentials that may be measured within brain 13. However, local field potentials may include a broader genus of electrical signals within brain 13 of patient 12.

In some examples, processor 50 accesses memory 52 to retrieve one or more previously recorded biosignals that are stored in memory 52. Processor 50 may compare the detected biosignal to one or more previously recorded biosignals. For example, processor 50 may compare a particular characteristic of the detected biosignal to the same characteristic (e.g., a signature biosignal characteristic) of the previously recorded biosignals. Example signal characteristics that can be compared include, but are not limited to, a power level within one or more frequency bands, a ratio of power levels within two or more frequency bands, a peak, average or lowest biosignal amplitude within a particular range of time, a characteristic waveform of the biosignal (e.g. "saw-tooth" wave forms from an EEG signal), a pattern in a biosignal amplitude over time, and the like.

In addition to or instead of monitoring biosignals of patient 12 via electrodes 22 coupled to lead 20, processor 50 may directly or indirectly receive biosignals indicative of electrical activity within brain 13 from electrodes coupled to another lead that is electrically coupled to sensing module 55, biosignals from electrodes coupled to an outer housing of IMD 16 and electrically coupled to sensing module 55, and/or biosignals from a sensing module that is separate from IMD 16.

In some examples, processor 50 may monitor and detect the physical movement of patient 12 via sensing module 55. For example, in some cases, sensing module 55 may include or be coupled to one or more accelerometer sensors capable of detecting patient movement and/or posture. Such accelerometer sensors may be contained in IMD 16 and/or may be located remotely at one or more locations within or on patient 12. Processor 50 may analyze the accelerometer sensor signals to detect physical movement of patient 12. Additionally or alternatively, sensing module 55 may be configured to generate an electromyography (EMG) signal to allow processor 50 to monitor the muscle tone of patient 12. In each case, processor 50 may detect the physical movement of patient 12 via sensing module 55.

In the example shown in FIG. 2, processor 50 may select one or more therapy programs from memory 52 to define the electrical stimulation delivered to patient 12 to treat symptoms of patient 12. Alternatively, programmer 14 may store one or more therapy programs, and processor 50 of IMD 16 may receive selected programs from programmer 14 via telemetry module 56. For example, processor 70 of programmer 14 (FIG. 3) may select one or more therapy programs from memory 72 and transmit the selected therapy program(s) to processor 50, which may then control stimulation generator 54 to deliver therapy according to the selected therapy program(s).

As described above, in the case of electrical stimulation therapy, each of the programs stored in memory 52 may include respective values for a plurality of therapy parameters, such as, e.g., voltage or current amplitude, signal duration, frequency, and electrode configuration (e.g., an indication of the electrodes 22 selected to deliver stimulation and the respective polarity of the electrodes). The therapy programs stored in memory 52 may be generated using programmer 14, e.g., during an initial or follow-up programming session, and received by processor 50 from programmer 14 via telemetry module 56.

Processor 50 controls telemetry module 56 to send information to and receive information from one or more devices external to IMD 16. Telemetry module 56 in IMD 16, as well as telemetry modules in other devices and systems described herein, such as programmer 14, may accomplish communication by RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request by IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time. In one example, power source 58 may be a 2.4 voltage (Volt) or 3.2 Volt rechargeable battery with a capacity of 12 milliamp hour (mAhr).

Memory 52 may store data relating to patient 12, such as the patient's name and age, the type of IMD 16 or leads 20 implanted within patient 12, medication prescribed to patient 12, and the like. Processor 50 of IMD 16 may also collect diagnostic information and store diagnostic information within memory 52 for future retrieval by a clinician. Diagnostic information may include other information or activities indicated by patient 12 using programmer 14, such as changes in symptoms, medication ingestion, or other activities of patient 12. A clinician may review the diagnostic information in a variety of forms, such as timing diagrams or a graph resulting from statistical analysis of diagnostic information, e.g., a bar graph. The clinician may, for example, download diagnostic information from IMD 16 via programmer 14 or another computing device. Diagnostic information may also include calibration routines for electrodes 22 (FIG. 1) and malfunction algorithms to identify stimulation dysfunctions.

According to this disclosure, processor 50 may generate control signals that control the shape of waveform pulses generated by stimulation generator 54. For example, processor 50 may generate a baseline current amplitude control signal that controls the baseline current amplitude of the resulting stimulation current generated by stimulation generator 54. As another example, processor 50 may generate a signal such that the signal causes the stimulation generator 54 to generate a stimulation pulse having a selected pulse shape. For example, processor 50 may store a sequence of program codes corresponding to the selected pulse shape in a memory (e.g., memory 52 or another memory not shown) that is accessible by stimulation generator 54. Stimulation generator 54 may be configured to retrieve one or more program codes within the sequence of program codes from the memory, and generate the stimulation current pulse such that the stimulation current pulse has an amplitude that is determined at least in part on the retrieved one or more program codes. In some cases, the stimulation generator 54 may include a CAPDAC, and be configured to modify the state of the CAPDAC based on the sequence of program codes.

In some examples, stimulation generator 54 may be configured to generate the stimulation current pulse such that a fixed component of the stimulation current pulse is controlled by a sampled amplitude of the first signal and a time-varying component of the stimulation current pulse is controlled by a second signal that varies with respect to time during the stimulation pulse. In some examples, the second signal may be the sequence of program codes stored in the memory.

In further examples, stimulation generator 54 may include a signal generator that is configured to generate a signal to control a baseline amplitude component of the output current. In such examples, stimulation generator 54 may be configured to sample the signal, and power down at least a portion of the signal generator during delivery of at least part of the stimulation pulse. In some implementations, the signal generator may be a resistive DAC.

Figure 3:
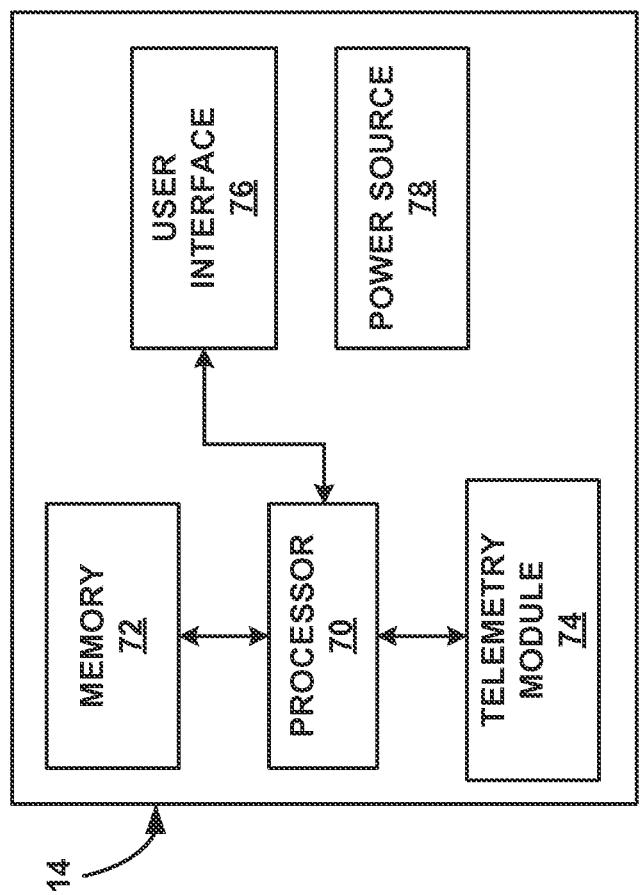
FIG. 3 is a functional block diagram illustrating the example medical device programmer of FIG. 1 in greater detail.

FIG. 3 is a conceptual block diagram of the example external medical device programmer 14 of FIG. 1 in greater detail. External medical device programmer 14 includes a processor 70, a memory 72, a telemetry module 74, a user interface 76, and a power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

Processor 70 monitors user activity from user interface 76 via one or more input controls, and controls the display of user interface 76 based on the monitored activity. The user, such as a clinician or patient 12, may interact with programmer 14 through user interface 76. User interface 76 may include a display (not shown), such as an LCD or other type of screen, to present information related to the therapy, and input controls (not shown) to provide input to programmer 14. Input controls may include buttons, a keypad (e.g., an alphanumeric keypad), a peripheral pointing device, or another input mechanism that allows the user to navigate through the user interface of programmer 14 and to provide input. If programmer 14 includes buttons and a keypad, then one or more of the buttons may, in some cases, be dedicated to performing a certain function, e.g., a power button. In additional cases, one or more of the buttons and/or the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or sounds to patient 12 and/or for receiving voice commands from patient 12, which may be useful if patient 12 has limited motor functions.

In some examples, at least some of the control of therapy delivery by IMD 16 may be implemented by processor 70 of programmer 14. For example, processor 70 may, in some examples, receive a biosignal from IMD 16 or from a sensing module that is separate from IMD 16, where the biosignal is sensed within brain 13 by IMD 16 or the sensing module that is separate from IMD 16. The separate sensing module may, but need not be, implanted within patient 12. Processor 50 of IMD 16 may receive the signal from programmer 14 via telemetry communication. Patient 12, a clinician or another user may also interact with programmer 14 to manually select therapy programs, generate new therapy programs, modify therapy programs through individual or global adjustments, and transmit the new programs to IMD 16.

Memory 72 may include instructions for operating user interface 76, telemetry module 74 and managing power source 78. Memory 72 may also store any therapy data retrieved from IMD 16 during the course of therapy. The clinician may use this therapy data to determine the progression of the patient condition in order to predict future treatment. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Memory 72 may be considered, in some examples, a non-transitory computer-readable storage medium comprising instructions that cause one or more processors, such as, e.g., processor 70, to implement one or more of the example techniques described in this disclosure. As one example, memory 72 may be removed from programmer 14, and moved to another device.

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to telemetry module 56 of IMD 16. In alternative examples, programmer 14 may be capable of infrared communication or direct communication through a wired connection. In this manner, other external devices may be capable of communicating with programmer 14 without needing to establish a secure wireless connection.

Power source 78 delivers operating power to the components of programmer 14. Power source 78 may include a battery and a power generation circuit to produce the operating power. In some examples, the battery may be rechargeable to allow extended operation. Recharging may be accomplished, for example, by electrically coupling power source 78 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 78 may include circuitry to monitor power remaining within a battery. In this manner, user interface 76 may provide a current battery level indicator or low battery level indicator when the battery needs to be replaced or recharged. In some cases, power source 78 may be capable of estimating the remaining time of operation using the current battery.

Figure 4A:
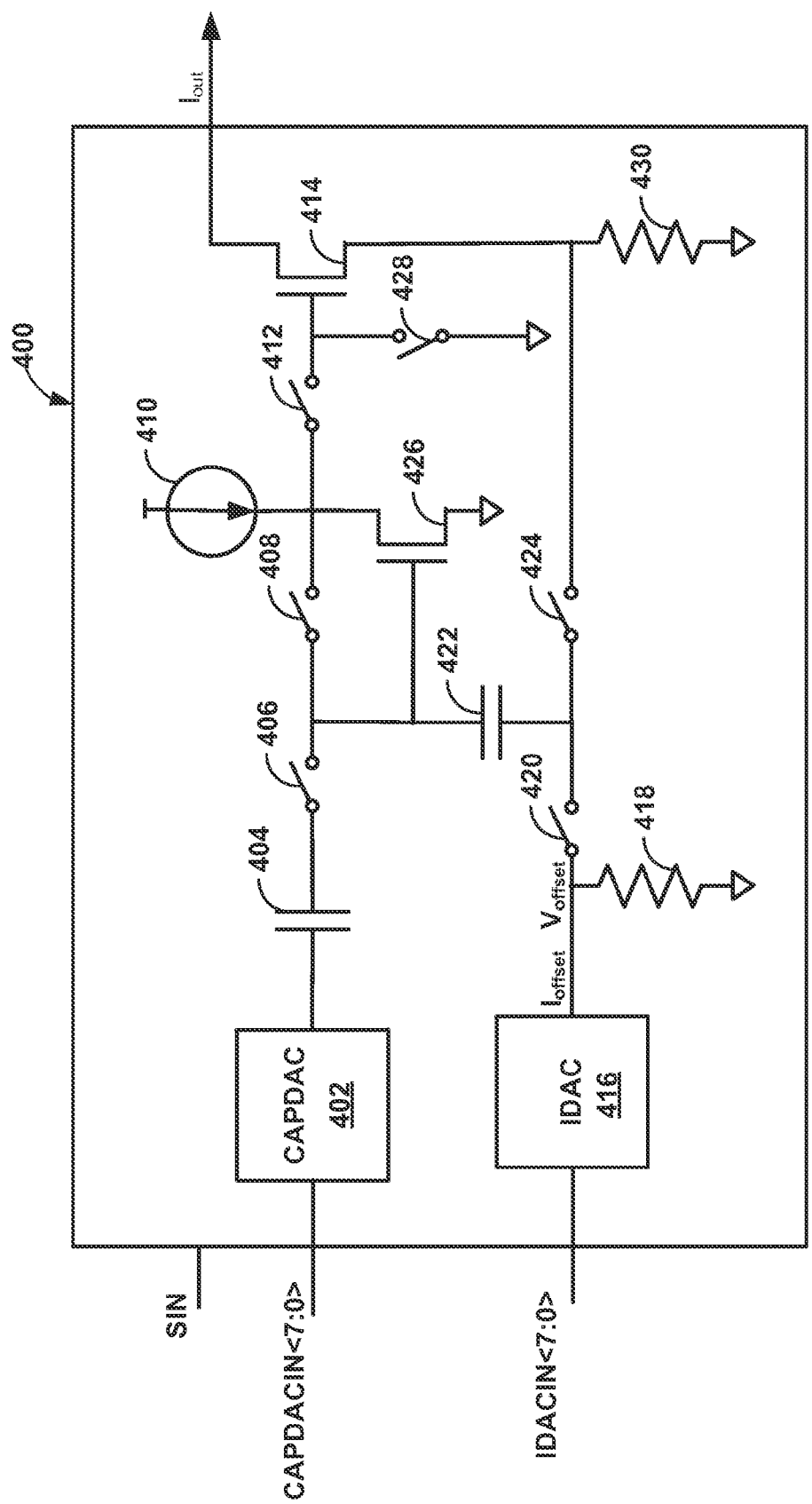
FIG. 4A is schematic diagram illustrating an example stimulation generator circuit in accordance with this disclosure.

FIG. 4A is a schematic diagram illustrating an example stimulation generator circuit 400 in accordance with this disclosure. The example stimulation generator circuit 400 in FIG. 4A may be used to implement all or part of the stimulation generator 54 shown in FIG. 2. Stimulation generator circuit 400 is configured to receive one or more switch control signals (SIN), a CAPDAC control signal (CAPDACIN), and a IDAC control signal (IDACIN) as input, and to output a stimulation current ($I_{out}$). In some examples, stimulation generator circuit 400 may be configured to sample an amplitude of a first signal (e.g., $V_{offset}$), receive a second signal that varies with respect to time (e.g., CAPDACIN), and generate a stimulation current pulse having an amplitude that is determined based on the sampled amplitude of the first signal and the second signal. The amplitude of the stimulation current pulse may vary with respect to time based on the second signal. Stimulation generator circuit 400 includes a CAPDAC 402, a capacitor 404, switches 406, 408, a bias current source 410, a switch 412, a transistor 414, an IDAC 416, an offset resistor 418, a switch 420, a capacitor 422, a switch 424, a transistor 426, a switch 428, and a sense resistor 430.

CAPDAC 402 is configured to receive the CAPDAC control signal as input, and modify the state of the CAPADAC based on the CAPDAC control signal. In some examples, the CAPDAC control signal may be a sequence of program codes that corresponds to a particular pulse shape, and CAPDAC 402 may sequentially modify the state of CAPDAC 402 based on the sequence of program codes. In such examples, each of the program codes may be selected from a set of program codes where each program code in the set of program codes may correspond to a particular incremental amplitude level for the output current, which may be added to or subtracted from a baseline amplitude level of output current that is controlled by IDAC 416. The program codes may be stored in a memory, such as memory 52 shown in FIG. 2 or another memory, and CAPDAC 402 may retrieve one or more of the program codes from the memory based on a timing controller (not shown). A control unit, such as processor 50 in FIG. 2, may program CAPDAC 402 to generate a particular sequence of incremental current amplitude levels corresponding to a particular pulse shape by placing a sequence of program codes into the memory that correspond to the particular pulse shape. The CAPDAC control signal shown in the example of FIG. 4A is an 8-bit control signal although other signals having the same or a different number of bits may be used in other examples. An output terminal of CAPDAC 402 is electrically coupled to a first terminal of capacitor 404.

CAPDAC 402 may include a plurality of capacitors each of which may have a terminal that may be selectively switched between a high voltage and a low voltage. The state of the switches for each of the capacitors in CAPDAC 402 may be modified based on CAPDAC control signal. During a stimulation phase, CAPDAC 402, capacitor 404 and capacitor 422 may form a capacitance network, and CAPDAC 402 may modulate (e.g., adjust and/or modify) the charge distribution among the different capacitors in the capacitance network based on the switching state of CAPDAC 402.

Capacitor 404 is configured to bias the least significant bit of CAPDAC 402 to a particular value. A first terminal of capacitor 404 is electrically coupled to an output terminal of CAPDAC 402, and a second terminal of capacitor 404 is electrically coupled to a first terminal of switch 406. In one example, capacitor 404 has a value of 1.5 pF.

Switches 406, 408, 412, 420, 424 and 428 are configured to couple and decouple portions of stimulation generator circuit 400 during various phases of operation based on the one or more switch control signals (SIN). Although not explicitly shown in FIG. 4A, each of 406, 408, 412, 420, 424 and 428 may be electrically coupled to one of the switch control signals (SIN). The switch control signals (SIN) may be controlled by a control unit, e.g., processor 50 in FIG. 2 or a dedicated control unit located within stimulation generator 54 in FIG. 2 (not shown) and/or within stimulation generator circuit 400 of FIG. 4A.

The control unit may cause switches 406, 408, 420 and 428 to be closed during a precharge phase, and switches 412 and 424 to be open during the precharge phase. The control unit may cause switches 412 and 424 to be closed during a stimulation phase, and switches 408, 420 and 428 to be open during the stimulation phase. During the stimulation phase, the control unit may, in some examples, cause switch 406 to be opened when the state of CAPDAC 402 is being updated to avoid transient charge distribution from affecting the current output, and cause switch 406 to be closed when the state of CAPDAC 402 is not being updated. In one example, switch 406 may be opened for approximately 400 nS each time the CAPDAC control signal is updated from memory.

The switch control signals (SIN) may include one or more digital signals that provide a control bit for one or more switches. In some examples, each of switches may be electrically coupled to and independently controlled by an individual switch control signal. In further examples, switches 408, 420 and 428 may be electrically coupled to and controlled by a common first switch control signal, and switches 412 and 424 may be electrically coupled to and controlled by a common second switch control signal. In additional examples, switches 408, 412, 420, 424 and 428 may be electrically coupled to and controlled by a single common switch control signal. In such examples, switches 408, 420 and 428 may be configured to be closed in response to the common switch control signal being in a first state, and switches 412 and 424 may be configured to be open in response to the common switch control signal being in the first state. Similarly, in response to the common switch control signal being in the second state in such examples, switches 408, 420 and 428 may be configured to be opened, and switches 412 and 424 may be configured to be closed. In further examples, switch 406 may be electrically coupled to and controlled by a switch control signal that is different than the switch control signal(s) used to control the operation of switches 408, 412, 420, 424 and 428.

A first terminal of switch 406 is electrically coupled to a second terminal of capacitor 404. A second terminal of switch 406 is electrically coupled to a first terminal of switch 408, a gate terminal of transistor 426, and a first terminal of capacitor 422. A first terminal of switch 408 is electrically coupled to a second terminal of switch 406, a first terminal of capacitor 422, and a gate terminal of transistor 426. A second terminal of switch 408 is electrically coupled to an output terminal of current source 410, a drain terminal of transistor 426, and a first terminal of switch 412. A first terminal of switch 412 is electrically coupled to a second terminal of switch 408, an output terminal of current source 410, and a drain terminal of transistor 426. A second terminal of switch 412 is electrically coupled to a gate terminal of transistor 414, and to a first terminal of switch 428. A first terminal of switch 428 is electrically coupled to a second terminal of switch 412, and to a gate terminal of terminal of transistor 414. A second terminal of switch 428 is electrically coupled to a ground voltage terminal.

A first terminal of switch 420 is electrically coupled to an output of IDAC 416, and to a first terminal of resistor 418. A second terminal of switch 420 is electrically coupled to a second terminal of capacitor 422, and to a first terminal of switch 424. A first terminal of switch 424 is electrically coupled to a second terminal of switch 420 and to the second terminal of capacitor 422. A second terminal of switch 424 is electrically coupled to a drain terminal of transistor 414, and to a first terminal of resistor 430.

Current source 410 generates a bias current for biasing transistor 426. In some examples, the bias current may bias transistor 426 to operate within a linear operating mode. The output terminal of current source 410 may be electrically coupled to the drain terminal of transistor 426. In one example bias current is 20 µA.

Transistor 426 is configured to operate as a diode during the precharge phase, and as a common source, active load voltage amplifier during the stimulation phase. That is, during the precharge phase, transistor may operate as a diode and generate a gate-to-source voltage that corresponds to the amplitude of the bias current. During the stimulation phase, transistor 426 may act as a voltage-controlled voltage source where the gate-to-source voltage of transistor 426 controls the voltage at the drain of transistor 426. In general, when the gate-to-source voltage of transistor 426 increases, the output voltage at the drain of transistor 426 decreases, and when the gate-to-source voltage of transistor 426 decreases, the output voltage at the drain of transistor 426 increases. A drain terminal of transistor 426 is electrically coupled to an output terminal of current source 410. A gate terminal of transistor 426 is electrically coupled to a second terminal of switch 406, to a first terminal of capacitor 422, and to a first terminal of switch 408. A source terminal of transistor 426 is electrically coupled to a ground voltage terminal.

Transistor 414 is configured to operate in a cutoff operating mode during the precharge phase, and to operate in a linear operating mode during the stimulation phase. During the stimulation phase, transistor 414 may be configured to operate in common-drain, source follower configuration. During the stimulation phase, transistor 414 may output the output current ($I_{out}$) having a magnitude that is determined based on the voltage across resistor 430. The voltage across resistor 430 may refer to the voltage between a first terminal of resistor 430 and a second terminal of resistor 430, e.g., the voltage between the source of transistor 414 and a ground terminal. A drain terminal of transistor 414 is configured to provide the output current ($I_{out}$) for stimulation generator circuit 400. A gate terminal of transistor 414 is electrically coupled to a second terminal of switch 412, and to a first terminal of switch 408. A source terminal of transistor 414 is electrically coupled to a second terminal of switch 424, and to a first terminal of resistor 430.

In the example illustrated in FIG. 4A, transistors 414 and 426 are n-type MOSFET transistors. However, in other examples, p-type MOSFET transistors may be used and/or bipolar junction transistors (BJTs).

IDAC 416 receives the IDAC control signal (IDACIN) as an input signal, and outputs a corresponding offset current ($I_{offset}$) based on the IDAC control signal such that an offset voltage ($V_{offset}$) is generated across offset resistor 418. In some examples, the IDAC control signal may be generated by processor 50 in FIG. 2. For example, processor 50 may generate the IDAC control signal based on a selected stimulation pulse amplitude received from programmer 14. The selected stimulation pulse amplitude may form a baseline amplitude for the resulting stimulation current ($I_{out}$). The current output of IDAC 416 is electrically coupled to a first terminal of resistor 418 and to a first terminal of switch 420. In one example, IDAC 416 is a resistive digital-to-analog converter (DAC) that is configured to receive an 8-bit control signal (e.g., IDACIN<7:0>) and generate a current within a range of 781 nA to 200 µA in 781 nA increments.

Resistor 418 is configured to generate an offset voltage ($V_{offset}$) between a first terminal of resistor 418 and a second terminal of resistor 418 based on the offset current ($I_{offset}$) generated by IDAC 416. A first terminal of resistor 418 is electrically coupled to an output terminal of IDAC 416 and to a first terminal of switch 420. A second terminal of resistor 418 is electrically coupled to a ground voltage terminal. In some examples, IDAC 416 and resistor 418 may form a signal generator that generates voltage signals across resistor 418, which may be sampled by switch 420 and capacitor 422.

Capacitor 422 is configured to store a charge that is indicative of the offset voltage ($V_{offset}$) generated during the precharge phase. During the stimulation phase, CAPDAC 402 may modulate the charge stored in capacitor 422 based on the CAPDAC control signal. In one example, capacitor 422 has a value of 10 pF. A first terminal of capacitor 422 is electrically coupled to a second terminal of switch 406, to a first terminal of switch 408, and to a gate terminal of transistor 426. A second terminal of capacitor 422 is electrically coupled to a second terminal of switch 420 and to a first terminal of switch 424.

Resistor 430 is configured to generate a current through resistor 430 based on a voltage formed across resistor 430. The amplitude of the output current ($I_{out}$) of transistor 414 may be determined based on the amplitude of the current flowing through resistor 430. A first terminal of resistor 430 is electrically coupled to a second terminal of switch 424, and to a source terminal of transistor 414. A second terminal of resistor 430 is electrically coupled to a ground voltage terminal. In some examples, resistor 430 may be a single resistor having a fixed resistance value. In further examples, resistor 430 may include of a network of resistors having fixed resistance values. In further examples, resistor 430 may be a variable resistance element configured to vary the resistance between the source of transistor 414 and the ground terminal based on a control signal. An example variable resistance element is described with respect to FIG. 6.

During operation, stimulation generator circuit 400 is controlled to cycle between a precharge phase and stimulation phase. In some examples, for each stimulation pulse delivered, stimulation generator circuit 400 may initially operate in the precharge phase during which a stimulation pulse is not delivered, and then switch to operating in a stimulation phase during which a stimulation pulse is delivered. At the end of the delivery of the stimulation pulse, stimulation generator circuit 400 may switch back to operating in the precharge phase to prepare for the delivery of the next stimulation pulse. A control unit may control the operation of stimulation generator circuit 400 by using the switch control signals (SIN). In some examples, the control unit may be processor 50 shown in FIG. 2. In other examples, the control unit may be located in stimulation generator 54 of FIG. 2 (not shown). The operation of stimulation generator circuit 400 during the precharge and stimulation phases will be described with respect to FIG. 4B and FIG. 4C.

Figure 4B:
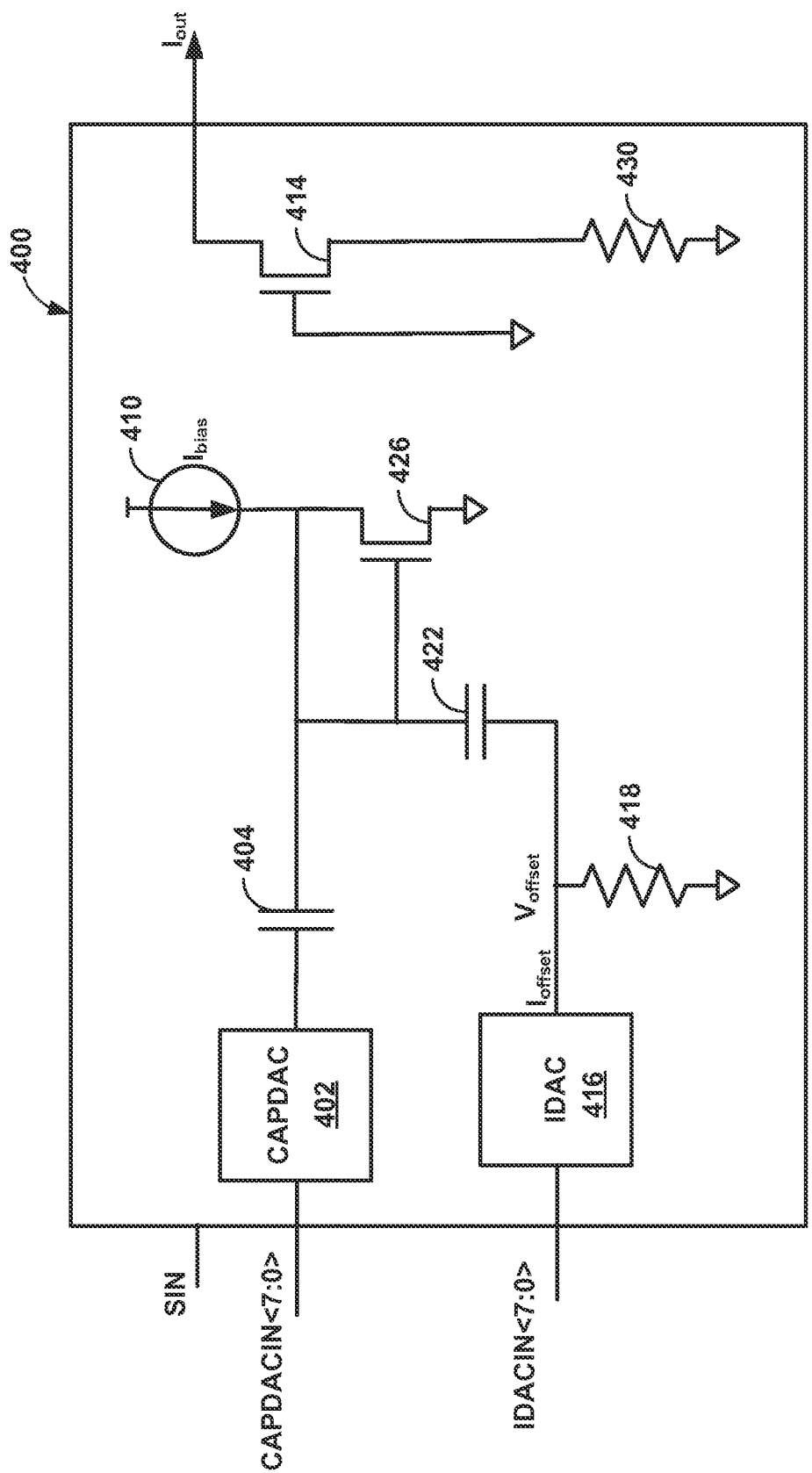
FIG. 4B is schematic diagram illustrating the example stimulation generator circuit during a precharge phase in accordance with this disclosure.

FIG. 4B is schematic diagram illustrating the stimulation generator circuit 400 during a precharge phase. During the precharge phase, switches 406, 408, 420, and 428 shown in FIG. 4A are closed, and switches 412 and 424 shown in FIG. 4A are open. Closing switch 420 causes the offset voltage signal ($V_{offset}$) to be electrically coupled to the second terminal of capacitor 422. As shown in FIG. 4B, transistor 426 is configured to act as a diode, and carries the bias current ($I_{bias}$). The gate-to-source voltage of transistor 426 may be biased to a particular level based on the amplitude of the bias current generated by current source 410. For example, the gate-to-source voltage of transistor 426 may be biased to a level where transistor 426 will operate in a linear operating mode during the corresponding stimulation phase. Transistor 414 is configured to operate in a cutoff operation mode, and does not generate a stimulation current during the precharge phase.

During the precharge phase, IDAC 416 is programmed to output an offset current ($I_{offset}$). Resistor 418 converts the offset current into an offset voltage ($V_{offset}$) between the two terminals of resistor 418. Because switch 420 is closed, capacitor 422 is charged such that capacitor 422 stores a resulting charge indicative of the amplitude of the offset voltage signal ($V_{offset}$), which is also indicative of the offset current ($I_{offset}$). For example, capacitor 422 may store a charge indicative of the voltage difference between the offset voltage ($V_{offset}$) and the gate of transistor 426 when biased by the bias current ($I_{bias}$). The offset voltage determines a baseline amplitude of the stimulation current ($I_{out}$) to be output during a corresponding stimulation phase. In some examples, CAPDAC 402 may be configured to output a reference voltage so that a full scale output current at the electrode may be provided during the stimulation phase.

Figure 4C:
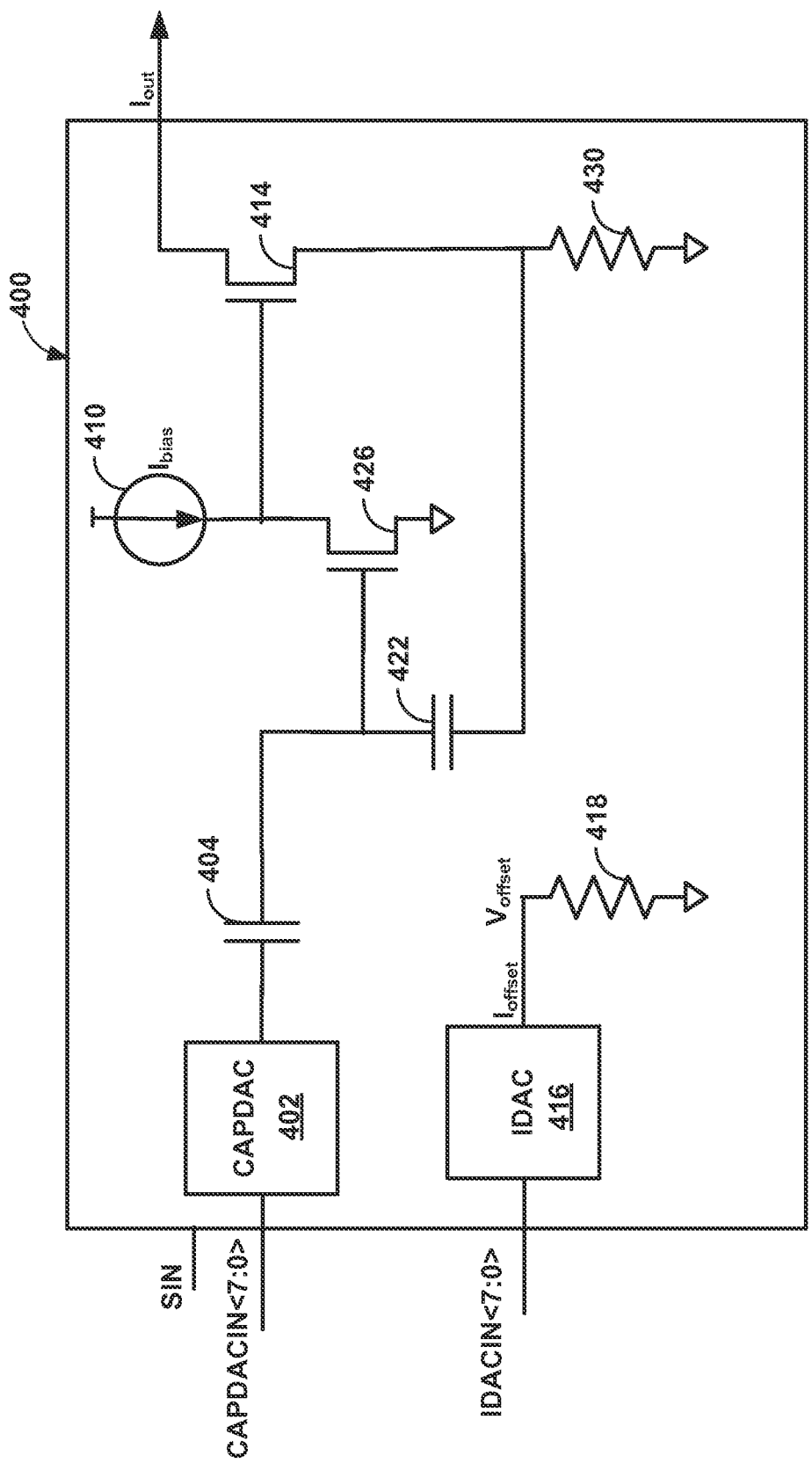
FIG. 4C is schematic diagram illustrating the example stimulation generator circuit during a stimulation phase in accordance with this disclosure.

FIG. 4C is schematic diagram illustrating the stimulation generator circuit 400 during a stimulation phase. During the stimulation phase, switches 412 and 424 are closed, and switches 408, 420 and 428 are open. Switch 406 may be opened and closed during the stimulation phase. For example, when the switching state of CAPDAC 402 is being modified, switch 406 may be opened to avoid transient charge distribution from affecting the current output. When the switching state of CAPDAC 402 is not being modified, switch 406 may be closed to cause CAPDAC 402 to control the time-varying portion of the output stimulation current pulse.

As shown in FIG. 4C, when operating in the stimulation phase, transistor 426 is configured to operate as a common-source, active load amplifier driven by the gate-to-source voltage of transistor 426. Transistor 414 is configured to operate as a common-drain source follower, and may output an output current ($I_{out}$) having an amplitude that is determined based on the voltage across resistor 430. Because switch 424 is closed, a feedback loop is formed, which includes transistor 426, transistor 414, and capacitor 422. The feedback loop may also include a feedback path formed between capacitor 422 and resistor 430. When switch 406 is closed, a capacitance network is formed that includes the capacitors in CAPDAC 402, capacitor 404 and capacitor 422.

Upon switching from the precharge phase to the stimulation phase, switch 420 is opened causing the offset voltage signal ($V_{offset}$) to be decoupled from the second terminal of capacitor 422. Because capacitor 422 stores a charge indicative of the offset voltage signal ($V_{offset}$) at the time switch 420 is opened, capacitor 422 and switch 420 effectively samples the offset voltage signal ($V_{offset}$) at the time stimulation generator circuit 400 switches between the precharge phase and the stimulation phase, and applies the sampled voltage to the feedback path formed between capacitor 422 and resistor 430.

The feedback loop that includes transistor 426, transistor 414, and capacitor 422 causes the voltage across resistor 430 to be regulated at a target voltage level. For example, if the voltage across resistor 430 happens to decrease below the target voltage level, the feedback loop between the source of transistor 414 and the gate of transistor 426 may cause the gate voltage of transistor 426 to decrease. This in turn may cause the voltage at the gate of transistor 414 to increase, which may in turn cause the voltage across resistor 430 to increase back to the target voltage level. Similarly, if the voltage across resistor 430 happens to increase above the target voltage level, the feedback loop between the source of transistor 414 and the gate of transistor 426 may cause the gate voltage of transistor 426 to increase. This in turn may cause the voltage at the gate of transistor 414 to decrease, which may in turn cause the voltage across 430 to decrease back to the target voltage level.

The target voltage level may be a function of the charge stored in the capacitor 422. Initially, when the stimulation generator circuit 400 switches from the precharge phase to the stimulation phase, the target voltage level may correspond to the sampled offset voltage level ($V_{offset}$). The feedback loop may regulate the voltage across resistor 430 at the sampled offset voltage level ($V_{offset}$) until the state of CAPDAC 402 is changed.

The state of CAPDAC 402 may be modified in response to detecting a change in the CAPDAC control signal. For example, a new program code may be retrieved from a memory that is different than a previous program code. In some examples, stimulation generator circuit 406 may be configured to update the state of CAPDAC 402 at regular time intervals during the delivery of the stimulation pulse. Modifying the state of CAPDAC 402 may include opening and/or closing one or more switches associated with individual capacitors in the CAPDAC. In some examples, switch 406 may be opened when the state of CAPDAC 402 is being modified, and closed after the particular state modification is complete. In response to modifying the state of CAPDAC 406, the charges in the capacitors of the capacitance network formed by CAPDAC 402, capacitor 404, and capacitor 406 are redistributed based on the modified state of CAPDAC 402. In particular, the amount of charge stored in capacitor 422 may be modified and/or updated in response to modifying the state of CAPAC 402. Each state of CAPDAC 402 may be associated with an incremental current amplitude that may be added to or subtracted from a baseline current amplitude that corresponds to the offset voltage level ($V_{offset}$).

Because the target voltage level at which the feedback loop is regulated depends on the charge stored in capacitor 422, modifying the charge stored in capacitor 422 causes the target voltage level (i.e., the voltage across resistor 430) to be modified. In general, the target voltage level at which the feedback loop is regulated may be a function of the sampled amplitude of the offset voltage signal ($V_{offset}$) and the CAPDAC control signal. Modifying the target voltage level causes the amplitude of the output current ($I_{out}$) to be modified. Therefore, by modifying the state of CAPDAC 402, the amplitude of the output current ($I_{out}$) may be adjusted during the delivery of a stimulation pulse. For example, the amplitude of the output current ($I_{out}$) may be regulated at a target amplitude that is a function of a baseline current amplitude corresponding to the sampled offset voltage and an incremental current amplitude associated with the switching state of CAPDAC 402. In some examples, the output current ($I_{out}$) may be substantially equal to a sum of the baseline current amplitude corresponding to the sampled offset voltage and an incremental current amplitude associated with a particular switching state of CAPADAC 402. Each switching state of CAPDAC 402 may be associated with a particular value of the CAPDAC control signal, which may be monitored during the delivery of a simulation pulse. In this manner, the stimulation generator circuit 400 may be used to generate complex pulse shapes (e.g., steps, ramps, etc.) even though the baseline voltage ($V_{offset}$) and current ($I_{offset}$) may be decoupled for the output during the delivery of a stimulation pulse.

As discussed above, a signal generator may be formed by IDAC 416 and resistor 418. Because the signal output by such a signal generator is sampled at the transition from the precharge phase to the stimulation phase, the output of a such a signal generator may not necessarily affect the instantaneous amplitude of the output current ($I_{out}$) during the stimulation phase. Thus, in some examples, stimulation generator circuit 400 may be configured to power down at least a portion of the signal generator (e.g., IDAC 416) during delivery of at least part of a stimulation pulse and/or for the entire stimulation phase of stimulation generator circuit 400.

In another example, the amplitude of the stimulation current pulse may be varied during the stimulation phase by varying the resistance of resistor 430. In one example, resistor 430 may be a variable resistance element, such that the value of its resistance may be varied using a control signal generated by a processor or a control unit. In this manner, the resistance value of resistor 430 may be changed during the stimulation phase, thereby modulating the stimulation current. In one example, the resistance value of resistor 430 may be varied during the stimulation phase and the states of CAPDAC 402 may also be switched during the stimulation phase. In this manner, CAPDAC 402 may provide one set of incremental adjustments and resistor 430 may provide another set of equivalent, finer, or coarser incremental adjustments. In another example, stimulation current may be varied during a stimulation phase by varying the resistance of resistor 430 without necessarily modifying the state of and/or using CAPDAC 402 (e.g., switch 406 may be open during the stimulation phase, the state of CAPDAC 402 may not be switched during a stimulation phase, or a stimulation generator circuit 400 may be implemented without CAPDAC 402). In one example, stimulation generator circuit 400 may be configured such that decreasing the resistance of resistor 430 by one half during the stimulation pulse increases the amplitude of the current pulse by a factor of two.

Figure 5:
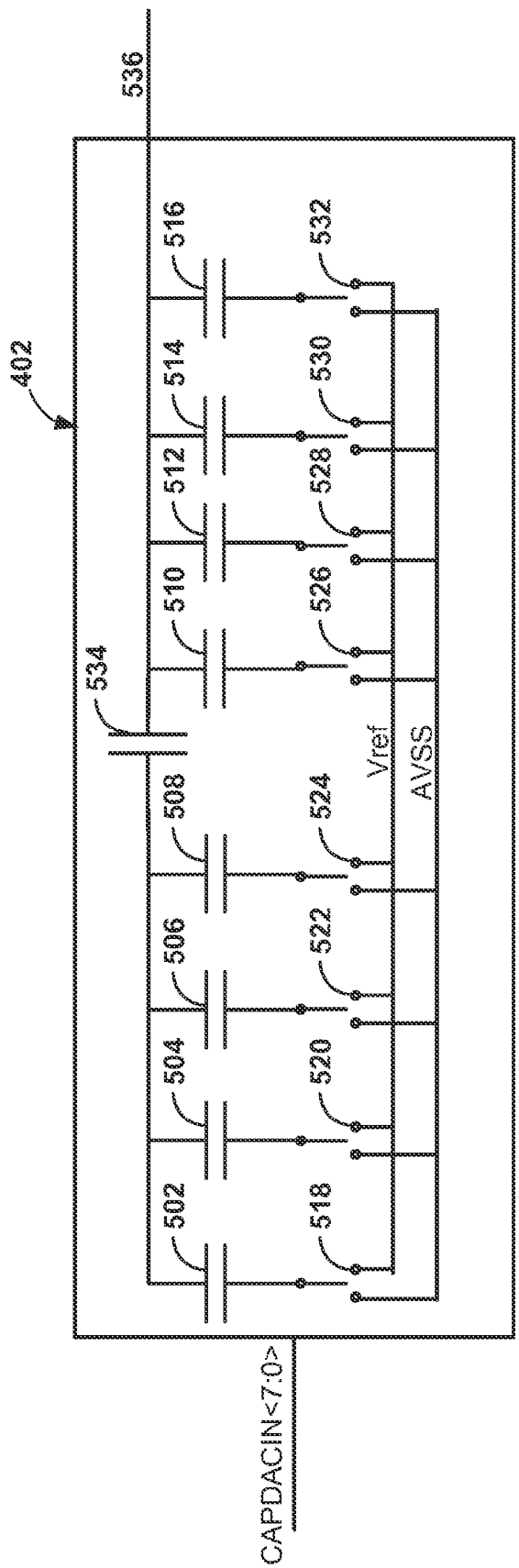
FIG. 5 is a schematic diagram illustrating an example capacitive digital-to-analog converter (CAPDAC) that may be used in the stimulation generator circuit of FIGS. 4A-4C.

FIG. 5 is a schematic diagram illustrating an example CAPDAC 402 that may be used in the stimulation generator circuit of FIGS. 4A-4C. CAPDAC 402 receives a CAPDAC control signal as input, and adjusts the internal switching state of CAPDAC 402 based on the control signal. CAPDAC 402 includes capacitors 502, 504, 506, 508, 510, 512, 514, 516 and switches 518, 520, 522, 524, 526, 528, 530, 532, capacitor 534 and an output terminal 536. Each of switches 520, 522, 524, 526, 528, 530, 532 electrically couples a respective one of capacitors 502, 504, 506, 508, 510, 512, 514, 516 to one of a reference voltage ($V_{ref}$) and an analog ground AVSS depending on the state of the respective switch.

In some examples example, the values of capacitors 502, 504, 506, 508, 510, 512, 514 and 516 may be scaled across CAPDAC 402 to provide an 8-bit DAC. For example, the values of capacitors 502 and 510 may be equal to a baseline capacitance ($C_0$), the values of capacitors 504 and 512 may be equal to $2C_0$, the values of capacitors 506 and 514 may be equal to $4C_0$, and the values of capacitors 508 and 516 may be equal to $8C_0$. Capacitor 534 causes the effective capacitive contribution of capacitors 502, 504, 506, and 508 to be multiplied relative to capacitors 510, 512, 514, and 516. In one example, capacitor 534 is a 16× multiplier. In one example, capacitor 534 is equal to 640 fF.

Each of switches 518, 520, 522, 524, 526, 528, 530, 532 may be switched into one of a first switching state and a second switching state. In the first switching state, each switch (e.g., switch 518) electrically couples a corresponding capacitor (e.g., capacitor 502) to a reference voltage ($V_{ref}$). In a second switching state, each switch (e.g., switch 518) electrically couples a corresponding capacitor (e.g., capacitor 502) to an analog ground AVSS depending on the state of the respective switch. The switching state of all of switches 518, 520, 522, 524, 526, 528, 530, 532 associated with all of capacitors 502, 504, 506, 508, 510, 512, 514, 516 in CAPDAC 402 may be referred to, in some examples, as the state of CAPDAC 402.

For each different state of CAPDAC 402, a different combination and/or configuration of weighted capacitors may be electrically coupled to output terminal 536. The combination and/or configuration of weighted capacitors associated with a particular state of CAPDAC 402 may form part of a capacitance network with other capacitors electrically coupled to output terminal 536 (e.g., capacitors 404, 422 in FIG. 4C). When the state of CAPDAC 402 is changed, the charges in the capacitance network may be redistributed amongst the capacitors in the capacitance network. As discussed above with respect to FIGS. 4A-4C, the amplitude of the resulting baseline current may be modulated based on the charge distribution in the capacitance network, and in particular, the charge stored in capacitor 422 of FIG. 4C. Therefore, each state of CAPDAC 402 may be associated with a particular incremental current amplitude that is either added or subtracted to a baseline or fixed current amplitude. In some examples, CAPDAC 402 may be configured to adjust the current in 50 uA incremental adjustments to stimulation current during a stimulation phase where the baseline current is between 50 uA and 12.75 mA.

During a precharge phase, output node 536 may be initialized to reference voltage so that a full scale output current is provided during the stimulation phase. During the stimulation phase, different switching states for CAPDAC 402 may be stepped through according to CAPDAC control signal, in effect transferring charge to, or from, capacitor 422 and incrementally adjusting the stimulation current.

Figure 6:
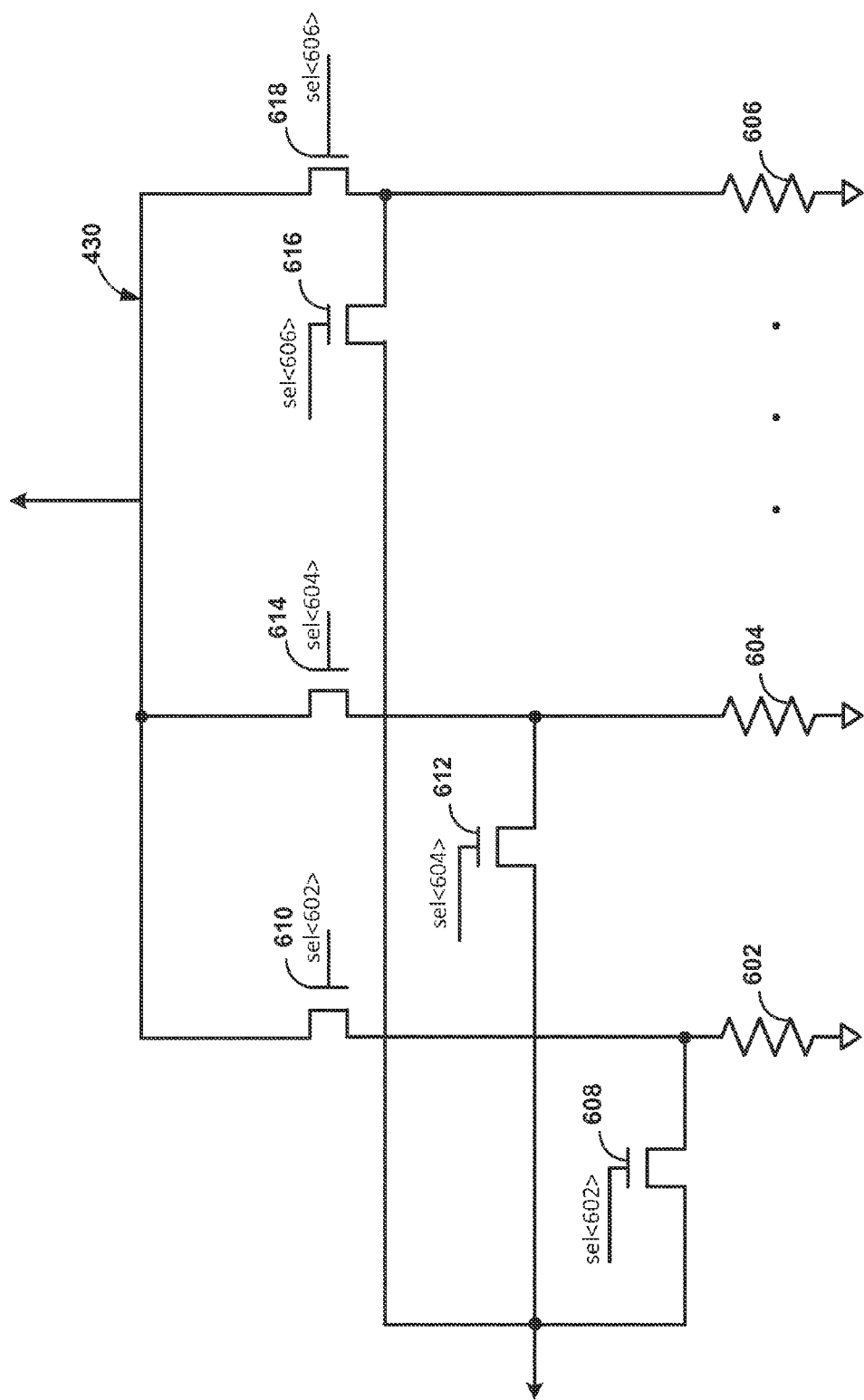
FIG. 6 is a schematic diagram illustrating an example resistive element that may be used in the stimulation generator circuit of FIGS. 4A-4C.

FIG. 6 is a schematic diagram illustrating an example of a variable resistive element that may be used in some examples for resistor 430. In the example, shown in FIG. 6 resistor 430 receives a control signal and the equivalent resistance of 430 is modified accordingly. In the example shown in FIG. 6, resistor 430 includes resistors 602, 604, and 606; and switches 608, 610, 612, 614, 616 and 618. By opening and closing switches 608, 610, 612, 614, 616 and 618 during a stimulation phase according to a control signal (e.g.

sel<602>, sel<604>, and sel<606>) the equivalent value of resistor 430 may be varied thereby varying the amplitude of the stimulation current. In the example, shown in FIG. 6 the value of resistor 602 may be 24 ohms and the value of resistor 606 may be 6 kiloohms (Kohms) and any number of resistors with incremental values may be placed between resistor 602 and 606. In the example of FIG. 6, for the sake of brevity, only resistor 604 is shown. Further, in other examples, resistor 430 may comprise other resistive circuits that are configured to generate a resistance value based on either an analog or digital control signal.

Figure 7:
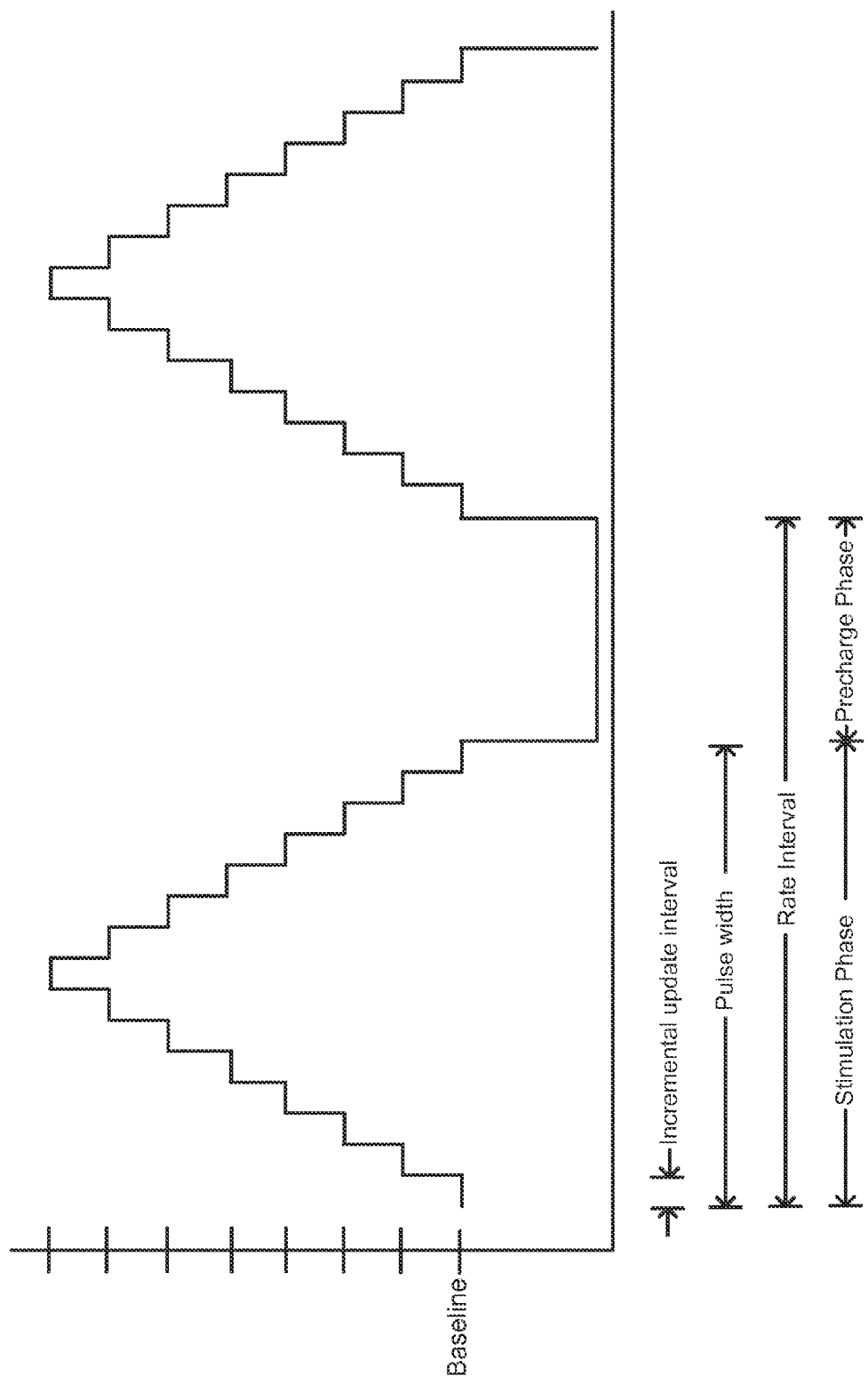
FIG. 7 is a conceptual graph illustrating an example stimulation current that may be generated by the example stimulation generation circuit of FIGS. 4A-4C.
Figure 8:
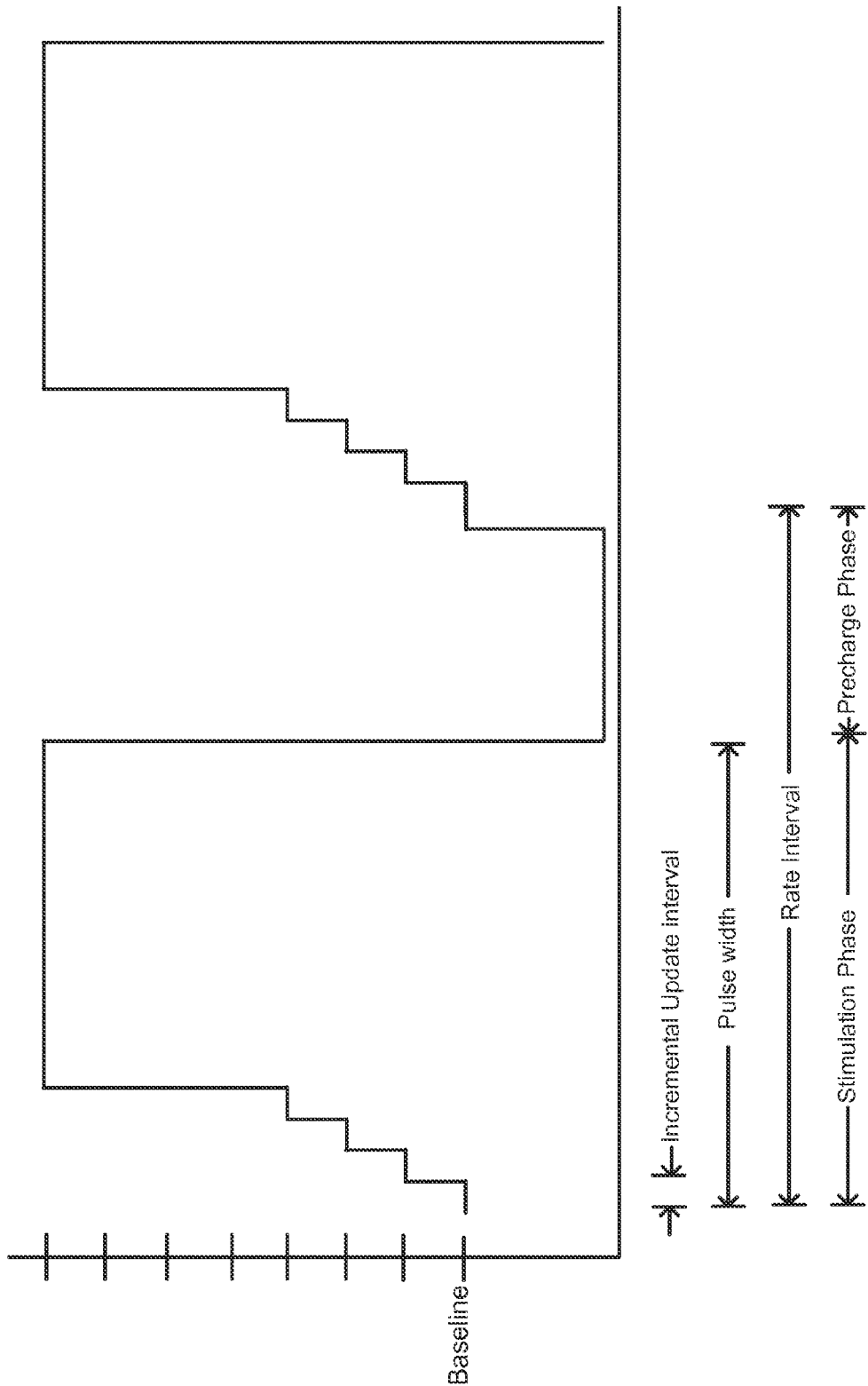
FIG. 8 is a conceptual diagram illustrating another example stimulation current that may be generated by the example stimulation generation circuit of FIGS. 4A-4C.
Figure 9:
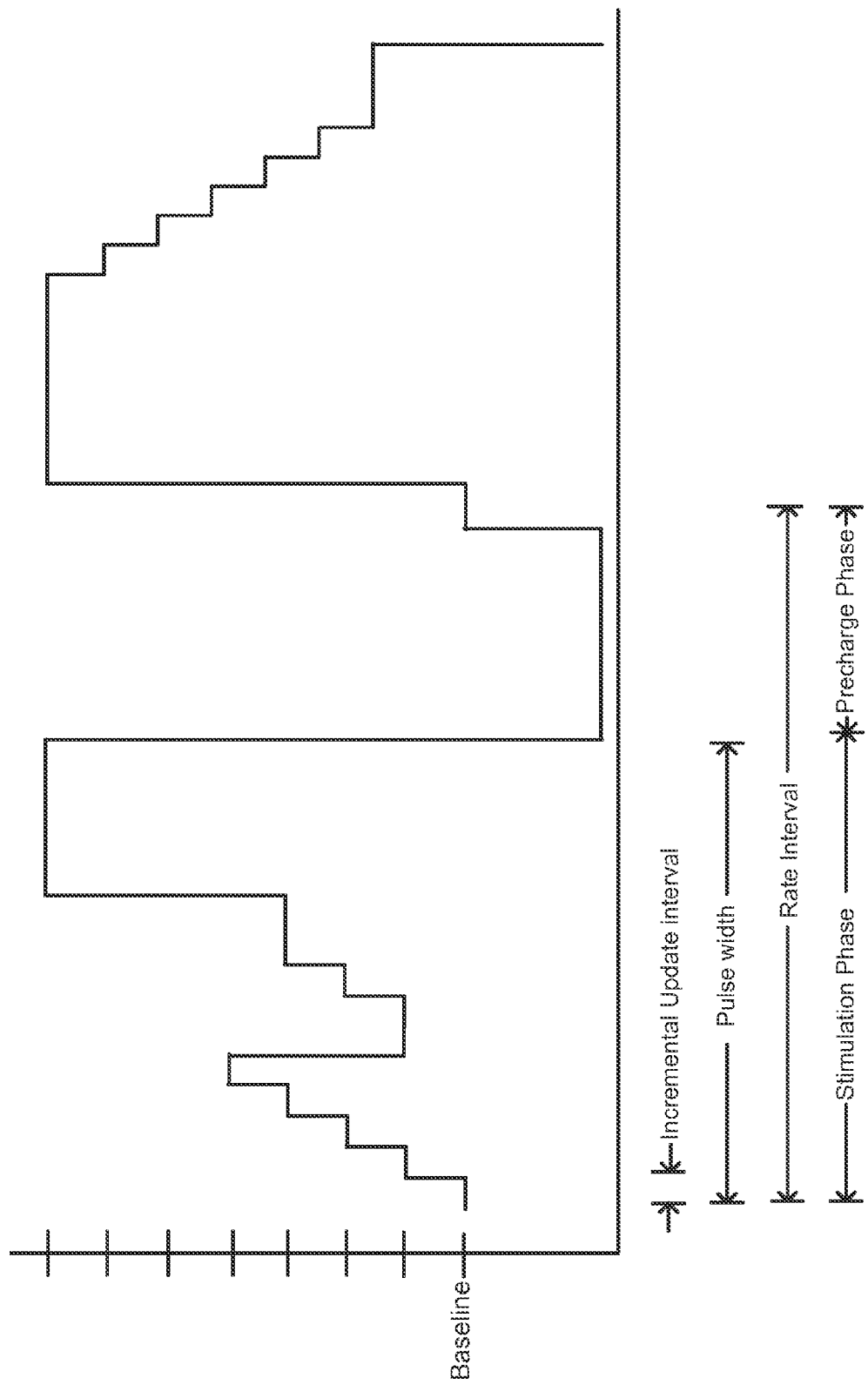
FIG. 9 is conceptual diagram illustrating another example stimulation current that may be generated by the example stimulation generation circuit of FIGS. 4A-4C.

FIGS. 7-9 are conceptual diagrams illustrating an example stimulation current that may be generated by the example stimulation generation circuit 400 of FIGS. 4A-4C. It should be noted that the graphs in FIGS. 7-9 are shown for purposes of illustrating ideal waveform pulse shapes and as such the values are not necessarily to scale. The example stimulation generation circuit 400 describe in accordance with FIG. 4A may control pulse width, the rate interval, the stimulation phase time interval, and precharge phase time interval by controlling the switching of switches 406, 408, 412, 420, 424 and 428 in stimulation generation circuit 400. The incremental update interval may be controlled by adjusting the frequency at which CAPDAC 402 is updated and switch 406 is opened and closed. In another example, the incremental update interval may be controlled by adjusting the frequency at which the value of resistor 430 is modified. FIG. 7 illustrates an example where stimulation generation circuit 400 generates a pulse train waveform where each of the pulses has a step shape. FIG. 8 illustrates an example where stimulation generation circuit 400 generates a pulse train waveform where each of the pulses has a ramp shape. FIG. 9 illustrates an example where stimulation generation circuit 400 generates a different pulse shape for each stimulation pulse. Any number of user defined stimulation pulse patterns may be defined. In some examples, a sequence of program codes corresponding to each of the different pulse shapes may be stored in memory 52.

Figure 10:
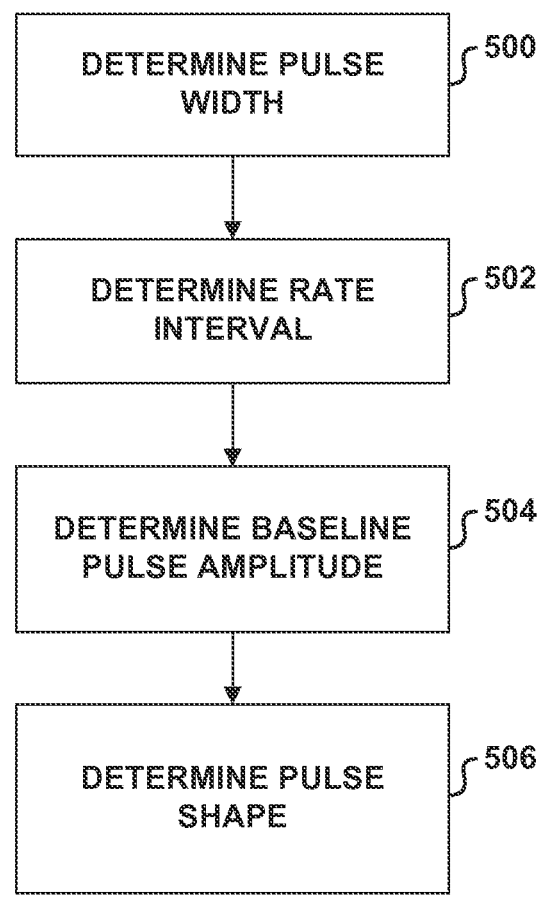
FIG. 10 is a flowchart illustrating an example technique for programming a medical device to generate a stimulation waveform.

FIG. 10 is a flowchart illustrating a technique for programming a medical device to generate stimulation waveforms according to the techniques describe in this disclosure. The example technique shown in FIG. 10 is described as being performed by programmer 14 of FIG. 1 for exemplary purposes. In other examples, one or more of the process boxes shown in FIG. 10 may be performed by one or more devices (e.g., IMD 16) in addition to or in lieu of programmer 14. Programmer 14 determines a stimulation pulse width (500). Programmer 14 determines a stimulation pulse interval rate (502). The switching of switches 406, 408, 412, 420, 424 and 428 of stimulation generation circuit 400 (FIGS. 4A-4C) may be controlled by the determined pulse width, and the switching of switches 406, 408, 412, 420, 424 and 428 of stimulation generation circuit 400 may be controlled by the determined pulse interval rate. Programmer 14 determines a baseline pulse amplitude (504). The IDACIN control signal that is fed into IDAC 416 of stimulation generation circuit 400 may be programmed to a particular value based on the determined baseline pulse amplitude. Programmer 14 determines a pulse shape (506). The CAPDACIN control signal that is fed into CAPDAC 402 of stimulation generation circuit 400 may be programmed to cycle through a sequence of program codes that correspond to the determined pulse shape.

Figure 11:
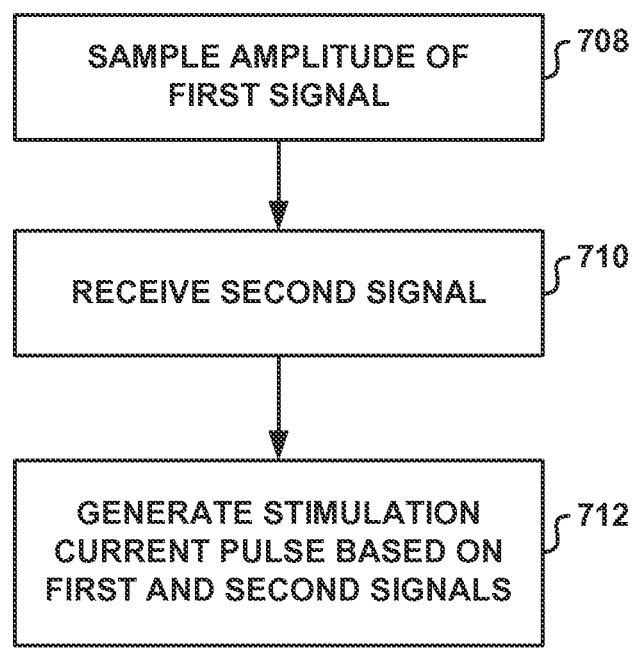
FIG. 11 is a flowchart illustrating an example technique for generating a stimulation current waveform in accordance with the techniques of this disclosure.

FIG. 11 is a flowchart illustrating an example technique for generating a stimulation current waveform in accordance with the techniques of this disclosure. The example technique shown in FIG. 11 is described as being performed by stimulation generator circuit 400 shown in FIGS. 4A-4C for exemplary purposes. However, in other examples, one or more of the process boxes shown in FIG. 11 may be performed by one or more components and/or circuits in addition to or in lieu of stimulation generator circuit 400.

Stimulation generator circuit 400 samples an amplitude of a first signal (708). Stimulation generator circuit 400 receives a second signal that varies with respect to time (710). The second signal may be a control signal that controls the state of CAPDAC 402, a control signal that controls the resistance value of resistor 430, or a set of two control signals where one control signal controls the state of CAPDAC 402 and the other control signal controls the resistance value of resistor 430. Stimulation generator circuit 400 generates a stimulation current pulse having an amplitude that is determined based on the sampled amplitude of the first signal and the second signal (712). The amplitude of the stimulation current pulse varying with respect to time based on the second signal.

Figure 12:
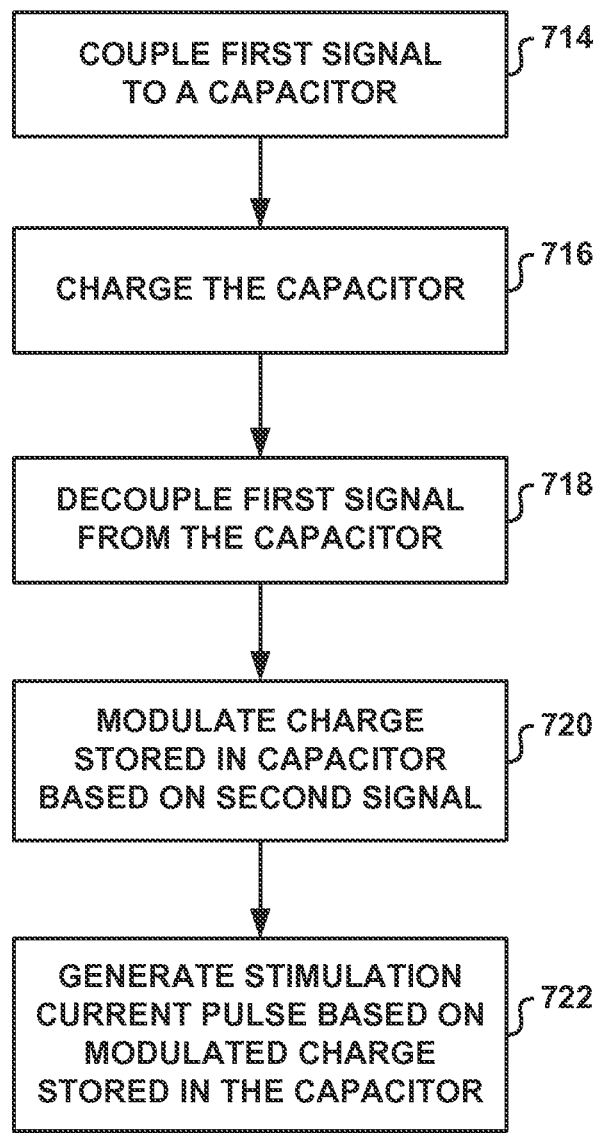
FIG. 12 is a flowchart illustrating another example technique for generating a stimulation current waveform in accordance with the techniques of this disclosure.

FIG. 12 is a flowchart illustrating another example technique for generating a stimulation current waveform in accordance with the techniques of this disclosure. The example technique shown in FIG. 12 is described as being performed by stimulation generator circuit 400 shown in FIGS. 4A-4C for exemplary purposes. However, in other examples, one or more of the process boxes shown in FIG. 12 may be performed by one or more components and/or circuits in addition to or in lieu of stimulation generator circuit 400.

During a precharge phase, switch 410 is closed and couples a first signal ($V_{offset}$) to a terminal of capacitor 422 (714). IDAC 416 charges capacitor 422 such that capacitor 422 stores an amount of charge indicative of the amplitude of the first signal ($V_{offset}$) (716). At a particular point in time, stimulation generator circuit 400 switches from the precharge phase to the stimulation phase. At that point in time, switch 410 is opened and decouples the first signal ($V_{offset}$) from capacitor 422 (718).

During the stimulation phase (e.g., after decoupling the first signal ($V_{offset}$) from the terminal of the capacitor 422 and while the first signal ($V_{offset}$) is decoupled from the capacitor 422), CAPDAC 402 modulates the charge stored in capacitor 422 based on a second signal (CAPDACIN) such that the capacitor stores a modulated amount of charge that is a function of the amplitude of the first signal at the point in time when the first signal is decoupled from capacitor 422 and a function of the second signal (720). The second signal may vary with respect to time during the delivery of a stimulation pulse, thereby causing the amount of charge stored in capacitor 422 to vary with respect to time during the delivery of a single stimulation pulse.

In some examples, the state of CAPDAC 402 may be modified based on the second signal (CAPDACIN) when the second signal is updated. In such examples, the capacitors in CAPDAC 402 along with capacitors 404 and 422 may form a capacitance network, and modifying the state of CAPDAC 402 may cause the charge within the capacitance network to be redistributed among the capacitors in the network. In particular, modifying the state of CAPDAC 402 may modulate (i.e., change or modify) the charge stored in capacitor 422. In other words, in such examples, the charge stored in capacitor 422 may be determined at least in part by the state of CAPDAC 422.

During the stimulation phase (e.g., while the first signal ($V_{offset}$) is decoupled from the capacitor 422), stimulation generator circuit 400 may generate the stimulation current pulse such that that the stimulation current pulse has an amplitude that is determined based on the modulated amount of charge stored in the capacitor 422 and that varies with respect to time based on the second signal (722). For example, the feedback loop formed by transistor 426, transistor 414 and capacitor 422 may regulate the voltage across resistor 430 at a voltage level that is a function of the charge stored in capacitor 422, and transistor 414 may output the stimulation current such that the stimulation current has an amplitude that is based on the regulated voltage level.

Although the techniques of this disclosure are described as being incorporated into an implantable medical device, the techniques of this disclosure may also be similarly applied to external medical devices that are not implanted in a patient. In addition, the example circuit architectures described herein that incorporate the techniques of this disclosure are shown as being current sinks for exemplary purposes. In other examples, the techniques of this disclosure may also be applied to current sources.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments of the invention have been described. These and other embodiments are within the scope of the following claims.

The invention claimed is:

1. A method comprising:
 storing a sequence of program codes corresponding to one or more pulse shapes in a memory;
 coupling a first signal to a terminal of a capacitor in a medical device;
 charging the capacitor such that the capacitor stores an amount of charge indicative of an amplitude of the first signal;
 decoupling the first signal from the terminal of the capacitor at a point in time;
 while the first signal is decoupled from the capacitor, modulating the amount of charge stored in the capacitor based on a second signal that varies with respect to time during delivery of a stimulation current pulse such that the capacitor stores a modulated amount of charge that is a function of the amplitude of the first signal at the point in time and a function of the second signal, wherein modulating the charge stored in the capacitor comprises modifying, based on the sequence of program codes, a state of a capacitive digital-to-analog converter (CAPDAC), wherein the CAPDAC is electrically coupled to the capacitor during delivery of at least part of the stimulation current pulse, the charge stored in the capacitor being determined at least in part by the state of the CAPDAC; and
 while the first signal is decoupled from the capacitor, generating the stimulation current pulse such that the stimulation current pulse has an amplitude that is determined based on the modulated amount of charge stored in the capacitor, wherein the second signal controls a time-varying amplitude component of the stimulation current pulse, and wherein the second signal causes the stimulation current pulse to have a pulse shape selected from the one more pulse shapes.

2. The method of claim 1, wherein the method further comprises:
 generating the first signal with a signal generator; and
 powering down at least a portion of the signal generator during delivery of at least part of the stimulation current pulse.

3. The method of claim 2, wherein the signal generator comprises a resistive digital-to-analog converter (DAC), and wherein powering down the at least the portion of the signal generator comprises powering down the resistive DAC during delivery of the at least part of the stimulation current pulse.

4. The method of claim 1, wherein generating the stimulation current pulse comprises generating the stimulation current pulse with a stimulation generator circuit, the method further comprising:
 receiving information indicative of a selected pulse shape; and
 generating the second signal such that the second signal causes the stimulation generator circuit to generate a stimulation pulse having the selected pulse shape.

5. The method of claim 4, further comprising:
 retrieving one or more program codes within the sequence of program codes from the memory; and
 generating the stimulation current pulse such that the stimulation current pulse has an amplitude that is determined at least in part on the retrieved one or more program codes.

6. The method of claim 1, wherein the capacitor is part of a feedback loop that regulates a voltage across a resistor at a voltage level that is a function of the modulated charge stored in the capacitor, and wherein generating the stimulation current pulse comprises generating the stimulation current pulse such that the stimulation current pulse has an amplitude that is based on the voltage level of the regulated voltage.

7. The method of claim 1, wherein the first signal is a voltage signal, wherein the method further comprises generating the voltage signal across a first resistor, and wherein generating the stimulation current pulse comprises:

regulating a voltage across a second resistor at an amplitude that is a function of an amplitude of the voltage signal at the point in time and the second signal, the amplitude of the stimulation current pulse being controlled by the amplitude of the regulated voltage.

8. The method of claim 1, further comprising:
outputting the stimulation current pulse via an output transistor, wherein the output transistor operates in a linear operating mode when the output transistor outputs the stimulation current pulse.

9. The method of claim 1, wherein the medical device is an implantable medical device, the method further comprising delivering the stimulation current pulse via one or more implantable electrodes.

10. The method of claim 9, wherein the one or more implantable electrodes are coupled to a distal end of one or more implantable leads, the proximal end of the one or more implantable leads being coupled to the implantable medical device, wherein delivering the stimulation current pulse comprises delivering the stimulation current pulse via the one or more implantable leads.

11. A medical device comprising:
a control unit configured to store, in a memory, a sequence of program codes corresponding to one or more pulse shapes;
a stimulation generator circuit comprising a capacitor, the stimulation generator circuit being configured to:
couple a first signal to a terminal of the capacitor;
charge the capacitor such that the capacitor stores an amount of charge indicative of an amplitude of the first signal;
decouple the first signal from the terminal of the capacitor at a point in time;
while the first signal is decoupled from the capacitor, modulate the amount of charge stored in the capacitor based on a second signal that varies with respect to time during delivery of a stimulation current pulse such that the capacitor stores a modulated amount of charge that is a function of the amplitude of the first signal at the point in time and a function of the second signal, wherein to modulate the charge stored in the capacitor the stimulation generator circuit modifies, based on the sequence of program codes, a state of a capacitive digital-to-analog converter (CAPDAC), wherein the CAPDAC is electrically coupled to the capacitor during delivery of at least part of the stimulation current pulse, the charge stored in the capacitor being determined at least in part by the state of the CAPDAC; and
while the first signal is decoupled from the capacitor, generate the stimulation current pulse such that the stimulation current pulse has an amplitude that is determined based on the modulated amount of charge stored in the capacitor and the second signal, wherein the second signal controls a time-varying amplitude component of the stimulation current pulse, and wherein the second signal causes the stimulation current pulse to have a pulse shape selected from the one more pulse shapes.

12. The medical device of claim 11, wherein the stimulation generator circuit comprises a signal generator configured to generate the first signal, and wherein the stimulation generator circuit is further configured to power down at least a portion of the signal generator during delivery of at least part of the stimulation current pulse.

13. The medical device of claim 12, wherein the signal generator comprises a resistive digital-to-analog converter (DAC), and wherein the stimulation generator circuit is further configured to power down the resistive DAC during delivery of the at least part of the stimulation current pulse.

14. The medical device of claim 11, wherein the control unit is further configured to receive information indicative of a selected pulse shape, and generate the second signal such that the second signal causes the stimulation generator circuit to generate a stimulation current pulse having the selected pulse shape.

15. The medical device of claim 14, wherein the stimulation generator circuit is further configured to retrieve one or more program codes within the sequence of program codes from the memory, and generate the stimulation current pulse such that the stimulation current pulse has an amplitude that is determined at least in part based on the retrieved one or more program codes.

16. The medical device of claim 11, wherein the stimulation generator circuit comprises a resistor and a feedback loop that includes the capacitor, the feedback loop being configured to regulate a voltage across the resistor at a voltage level that is a function of the modulated charge stored in the capacitor, and wherein the stimulation generator circuit is further configured to generate the stimulation current pulse such that the stimulation current pulse has an amplitude that is based on the voltage level of the regulated voltage.

17. The medical device of claim 11, wherein the first signal is a voltage signal, wherein the stimulation generator circuit comprises a first resistor and a second resistor, and wherein the stimulation generator circuit is further configured to generate the voltage signal across the first resistor, and regulate a voltage across a second resistor at an amplitude that is a function of an amplitude of the voltage signal at the point in time and the second signal, the amplitude of the stimulation current pulse being controlled by the amplitude of the regulated voltage.

18. The medical device of claim 11, wherein the stimulation generator circuit comprises an output transistor configured to output the stimulation current pulse, wherein the output transistor is configured to operate in a linear operating mode when the output transistor outputs the stimulation current pulse.

19. The device of claim 11, wherein the device is an implantable medical device configured to deliver the stimulation current pulse via one or more implantable electrodes.

20. The method of claim 19, wherein the one or more implantable electrodes are coupled to a distal end of one or more implantable leads, the proximal end of the one or more implantable leads being coupled to the implantable medical device, wherein the implantable medical device is further configured to deliver the stimulation current pulse via the one or more implantable leads.

21. A medical device comprising:
means for storing a sequence of program codes corresponding to one or more pulse shapes in a memory;
means for coupling a first signal to a terminal of a capacitor;
means for charging the capacitor such that the capacitor stores an amount of charge indicative of an amplitude of the first signal;
means for decoupling the first signal from the terminal of the capacitor at a point in time;
means for modulating, while the first signal is decoupled from the capacitor, the amount of charge stored in the capacitor based on a second signal that varies with respect to time during delivery of a stimulation current pulse such that the capacitor stores a modulated amount of charge that is a function of the amplitude of the first signal at the point in time and a function of the second signal, wherein the means for modulating the charge stored in the capacitor comprises means for modifying, based on the sequence of program codes, a state of a capacitive digital-to-analog converter (CAPDAC), wherein the CAPDAC is electrically coupled to the capacitor during delivery of at least part of the stimulation current pulse, the charge stored in the capacitor being determined at least in part by the state of the CAPDAC; and means for generating, while the first signal is decoupled from the capacitor, the stimulation current pulse such that the stimulation current pulse has an amplitude that is determined based on the modulated amount of charge stored in the capacitor and the second signal, wherein the second signal controls a time-varying amplitude component of the stimulation current pulse, and wherein the second signal causes the stimulation current pulse to have a pulse shape selected from the one more pulse shapes.

22. A method comprising:

storing a sequence of program codes corresponding to one or more pulse shapes in a memory;

generating a first signal with a signal generator, wherein the signal generator comprises a resistive digital-to-analog converter (DAC);

coupling the first signal to a terminal of a capacitor in a medical device;

charging the capacitor such that the capacitor stores an amount of charge indicative of an amplitude of the first signal;

decoupling the first signal from the terminal of the capacitor at a point in time;

while the first signal is decoupled from the capacitor, modulating the amount of charge stored in the capacitor based on a second signal that varies with respect to time during delivery of a stimulation current pulse such that the capacitor stores a modulated amount of charge that is a function of the amplitude of the first signal at the point in time and a function of the second signal; and while the first signal is decoupled from the capacitor, generating the stimulation current pulse such that the stimulation current pulse has an amplitude that is determined based on the modulated amount of charge stored in the capacitor, wherein the second signal controls a time-varying amplitude component of the stimulation current pulse, and wherein the second signal causes the stimulation current pulse to have a pulse shape selected from the one more pulse shapes;

powering down the resistive DAC to power down at least a portion of the signal generator during delivery of at least part of the stimulation current pulse.

23. The method of claim 22, wherein generating the stimulation current pulse comprises generating the stimulation current pulse with a stimulation generator circuit, the method further comprising:

receiving information indicative of a selected pulse shape; and generating the second signal such that the second signal causes the stimulation generator circuit to generate a stimulation pulse having the selected pulse shape.

24. The method of claim 22, wherein the capacitor is part of a feedback loop that regulates a voltage across a resistor at a voltage level that is a function of the modulated charge stored in the capacitor, and wherein generating the stimulation current pulse comprises generating the stimulation current pulse such that the stimulation current pulse has an amplitude that is based on the voltage level of the regulated voltage.

25. The method of claim 22, wherein the first signal is a voltage signal, wherein the method further comprises generating the voltage signal across a first resistor, and wherein generating the stimulation current pulse comprises:

regulating a voltage across a second resistor at an amplitude that is a function of an amplitude of the voltage signal at the point in time and the second signal, the amplitude of the stimulation current pulse being controlled by the amplitude of the regulated voltage.

26. The method of claim 22, further comprising:

outputting the stimulation current pulse via an output transistor, wherein the output transistor operates in a linear operating mode when the output transistor outputs the stimulation current pulse.

\* \* \* \* \*